US008883967B2

(12) United States Patent
Tomich et al.

(10) Patent No.: US 8,883,967 B2
(45) Date of Patent: Nov. 11, 2014

(54) BRANCHED AMPHIPATHIC OLIGO-PEPTIDES THAT SELF-ASSEMBLE INTO VESICLES

(75) Inventors: John M. Tomich, Manhattan, KS (US); Takeo Iwamoto, Manhattan, KS (US); Yasuaki Hiromasa, Manhattan, KS (US); Sushanth Gudlur, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 198 days.

(21) Appl. No.: 13/259,771

(22) PCT Filed: Mar. 26, 2010

(86) PCT No.: PCT/US2010/028916
§ 371 (c)(1),
(2), (4) Date: Sep. 23, 2011

(87) PCT Pub. No.: WO2010/111652
PCT Pub. Date: Sep. 30, 2010

(65) Prior Publication Data
US 2012/0021020 A1    Jan. 26, 2012

Related U.S. Application Data

(60) Provisional application No. 61/164,241, filed on Mar. 27, 2009.

(51) Int. Cl.
| | | |
|---|---|---|
| A61K 38/08 | (2006.01) |
| A61K 38/10 | (2006.01) |
| A61K 9/107 | (2006.01) |
| A61K 9/127 | (2006.01) |
| A61K 9/51 | (2006.01) |
| A61K 47/48 | (2006.01) |
| C07K 7/02 | (2006.01) |

(52) U.S. Cl.
CPC ............ *A61K 9/1075* (2013.01); *A61K 9/1273* (2013.01); *A61K 9/5169* (2013.01); *A61K 47/48038* (2013.01); *A61K 47/488* (2013.01); *C07K 7/02* (2013.01)
USPC ............ 530/329; 530/328; 530/330; 424/450

(58) Field of Classification Search
None
See application file for complete search history.

(56) References Cited

U.S. PATENT DOCUMENTS

| 5,368,712 | A | 11/1994 | Tomich et al. |
|---|---|---|---|
| 5,670,483 | A | 9/1997 | Zhang et al. |
| 5,882,645 | A | 3/1999 | Toth et al. |
| 5,955,343 | A | 9/1999 | Holmes et al. |
| 6,548,630 | B1 | 4/2003 | Zhang et al. |
| 6,576,254 | B1 | 6/2003 | Uchegbu |
| 6,800,481 | B1 | 10/2004 | Holmes et al. |
| 7,371,719 | B2 | 5/2008 | Stupp et al. |
| 7,452,679 | B2 | 11/2008 | Stupp et al. |
| 2003/0059906 | A1 | 3/2003 | Hubbell et al. |
| 2005/0208589 | A1 | 9/2005 | Stupp et al. |
| 2005/0209145 | A1* | 9/2005 | Stupp et al. ........... 514/12 |
| 2005/0272662 | A1 | 12/2005 | Stupp |
| 2007/0298494 | A1 | 12/2007 | Tomich et al. |
| 2009/0105449 | A1 | 4/2009 | Tomich et al. |
| 2012/0294902 | A1* | 11/2012 | Stupp et al. ............ 424/400 |

FOREIGN PATENT DOCUMENTS

| WO | 2006127048 A2 | 11/2006 | |
|---|---|---|---|
| WO | WO 2006127048 A2 * | 11/2006 | ............ C07K 14/47 |
| WO | 2010111652 A2 | 9/2010 | |

OTHER PUBLICATIONS

Roccatano et al., "Mechanism by which 2,2,2,-trifluoroethanol/water mixtures stabilize secondary-structure formation in peptides: A molecular dynamics study", PNAS, 2002, pp. 12179-12184.*
Segota et al. "Spontaneous formation of vesicles", Advances in Colloid and Interface Science, 2006, pp. 51-75.*
Sequence property calculation by GenScript at https://www.genscript.com/ssl-bin/site2/peptide_calculation.cgi for FLIVIGSIi; obtained Jun. 14, 2013; pp. 1-21.*
Sequence property calculation by GenScript at https://www.genscript.com/ssl-bin/site2/peptide_calculation.cgi for LPLGNSH; obtained Jun. 14, 2013; pp. 1-21.*
Sequence property calculation by GenScript at https://www.genscript.com/ssl-bin/site2/peptide_calculation.cgi for YPVHPST; obtained Jun. 14, 2013; pp. 1-21.*
Sequence property calculation by GenScript at https://www.genscript.com/ssl-bin/site2/peptide_calculation.cgi for for IKVAVK; obtained Jun. 14, 2013; pp. 1-21.*
Sequence property calculation by GenScript at https://www.genscript.com/ssl-bin/site2/peptide_calculation.cgi for for IKVAV; obtained Jun. 14, 2013; pp. 1-21.*
Sequence property calculation by GenScript at https://www.genscript.com/ssl-bin/site2/peptide_calculation.cgi forfor LLLAAAK; obtained Jun. 14, 2013; pp. 1-21.*
Xiaoqun Mo et al.; Article entitled "Design of 11-Residue Peptides with Unusual Biophysical Properties"; Induced Secondary Structure in the Absence of Water; Biophysical Journal vol. 94, pp. 1807-1817 (2008).

(Continued)

*Primary Examiner* — Karlheinz R Skowronek
*Assistant Examiner* — Lianko Garyu
(74) *Attorney, Agent, or Firm* — Hovey Williams LLP

(57) ABSTRACT

The present invention provides branched amphipathic peptides and vesicles formed thereof. The peptides comprise a polar/positively charged C-terminal segment, a branch point, and two hydrophobic N-terminal segments extending from the branch point. The vesicles are formed using a plurality of first and second peptides, wherein the first peptide has a different chain length from the second peptide. When a plurality of the first and second peptides are mixed together, they self-assemble to form small spheres defined by a membrane consisting of an interlocking peptide network bilayer and having a liquid-receiving interior space (i.e., hollow core). In the bi-layer, the respective hydrophobic segments of the peptides form beta-sheet structures having a hydrogen bond-stabilized, anti-parallel orientation in which the opposed sequences interlock to form a zipper-like structure in three dimensions. Thus, the peptide assembly (i.e., vesicle) can be held together at reduced concentrations where lipid vesicles would breakdown.

22 Claims, 13 Drawing Sheets

(56) References Cited

OTHER PUBLICATIONS

Bohdana M. Discher, You-Yeon Won, David S. Ege, James C-M. Lee, Frank S. Bates, Dennis E. Discher, and Daniel A. Hammer (1999) Polymersomes: Tough Vesicles Made from Diblock Copolymers Science 284 (5417): 1143-1146.

Checot, F., S. Lecommandoux, Y. Gnanou, H.-A. Klok (2002) Water soluble stimuli-responsive vesicles from peptide-based diblock copolymers Angew. Chem. Int. Ed., 2002 41(8), 1339-1343.

Checot, F., S. Lecommandoux, H.-A. Klok, Y. Gnanou (2003) From supramolecular polymersomes to stimuli-responsive nano-capsules based on poly(diene-b-peptide) diblock copolymers Eur. Phys. J E 10 (1) 25-35.

Holowka, E. P., D. J. Pochan, T. J. Deming (2005) Charged Polypeptide Vesicles with Controllable Diameter Journal of the American Chemical Society 127 (35): 12423-12428.

Bellomo, E.G., M. D. Wyrsta, L. Pakstis, D. J. Pochan and T. J. Deming (2004) Stimuli-responsive polypeptide vesicles by conformation-specific assembly Nature Materials 3: 244-248.

Santoso, S., W. Hwang, H. Hartman, S. Zhang (2002) Self-assembly of Surfactant-like Peptides with Variable Glycine Tails to Form Nanotubes and Nanovesicles Nano Letts. 2 (7), 687-691.

Mishra, A., J.J. Panda, A. Basu, . V. S. Chauhan (2008) Nanovesicles Based on Self-Assembly of Conformationally Constrained Aromatic Residue Containing Amphiphilic Dipeptides. Langmuir 24 (9),4571-4576.

Tanisaka H, Kizaka-Kondoh S, Makino A, Tanaka S, Hiraoka M, Kimura S. (2008) Near-infrared fluorescent labeled peptosome for application to cancer imaging. Bioconjug Chem. 19(1): 109-117.

Discher, D.E., A. Eisenberg (2002) Polymer Vesicles. Science 297(5583): 967-973.

Reches, M., E. Gazit (2004) Formation of Closed-Cage Nanostructures by Self-Assembly of Aromatic Dipeptides. Nano Letts. 4 (4), 581-585.

Grove, A., Tomich, J. M. and Montal, M. A molecular blueprint for the pore-forming structure of voltage gated calcium channels. (1991) Proc. Natl. Acad. Sci. USA.88, 6418-6422.

Grove, A., Tomich, J. M., Iwamoto, T. and Montal, M. (1993) Design of a functional calcium channel protein: Inferences about an ion channel forming motif derived from the primary structure of voltage-gated calcium channels. Protein Sci. 2, 1918-1930.

Whiles, J. A., R. Deems, R. R. Vold, E. A. Dennis (2002) Bicelles in structure-function studies of membrane-associated proteins. Bioorganic Chemistry 30:431-442.

Shen, Xinchun, Xiaoqun Mo, Robyn Moore, Shawnalea J. Frazier, Takeo Iwamoto, John M. Tomich, X Susan Sun (2006) Adhesion and Structure Properties of Protein Nanomaterials Containing Hydrophobic and Charged Amino Acids, Journal of Nanoscience and Nanotechnology, vol. 6, 837-844. PMID: 16573147.

Xiaoqun Mo, Yasuaki Hiromasa, Ahlam Al-Rawi Matt Warner, Takeo Iwamoto, Talat Rahman, Xiuzhi Sun and John M. Tomich. (2008) Design of II-Residue Peptides with Unusual Biophysical Properties: Induced Secondary Structure in the Absence of Water. Biophysical J. 94: 1807-1817.

Jeroen, J. L., M. Cornelissen, M. Fischer, A. Nico, J. M. Sommerdijk, J. M. Roeland Nolte (1998) Helical Superstructures from Charged Poly(styrene)-Poly(isocyanodipeptide) Block Copolymers Science 280 (5368): 1427.

International Preliminary Report on Patentability for PCT/US2010/028916, dated Sep. 27, 2011, 8 pages.

International Search Report & Written Opinion for PCT/US2010/028916, dated Jan. 25, 2011, 13 pages.

\* cited by examiner bis(h₉)-K-K₄

```
            + + + +
F L I V I G S I I K K K K
                  /      SEQ ID NO: 1
F L I V I G S I I
                         MW: 2568.72
      SEQ ID NO: 3
``` bis(h₅)-K-K₄

```
          + + + +
F L I V I K K K K
         /      SEQ ID NO: 1
F L I V I
                  MW: 1829.49
  SEQ ID NO: 4
``` bis(h₇)-K-K₄

```
              + + + +
V F F I V I L K K K K
             /      SEQ ID NO: 1
V F F I V I L
                     MW: 2321.53
   SEQ ID NO: 5
```

BRANCHED AMPHIPATHIC OLIGO-PEPTIDES THAT SELF-ASSEMBLE INTO VESICLES

CROSS-REFERENCE TO RELATED APPLICATIONS

This application is the National Stage of International Application No. PCT/US2010/028916, filed Mar. 26, 2010, which claims the priority benefit of a provisional application entitled BRANCHED AMPHIPATHIC OLIGO-PEPTIDES THAT SELF-ASSEMBLE INTO VESICLES, Ser. No. 61/164,241, filed Mar. 27, 2009, incorporated by reference herein in its entirety.

SEQUENCE LISTING

The following application contains a sequence listing in computer readable format (CRF), submitted as a text file in ASCII format entitled "Sequence Listing," created on Mar. 22, 2010, as 2 KB. The contents of the CRF are hereby incorporated by reference.

BACKGROUND OF THE INVENTION

1. Field of the Invention

The present invention relates in general to nano- and micro-structured vesicles having a novel bilayer membrane formed using branched, amphipathic peptides.

2. Description of the Prior Art

Since many drugs are rapidly destroyed or inactivated when introduced to the body, various strategies have been developed to improve delivery and increase the biological half-life of the bioactive materials. Current drug delivery methodologies that address these issues rely on several biomaterials as well as some inorganic molecules. Some of these materials include polyethylene glycol, micelles, lipid vesicles, viral capsids, and nanoparticles. More recently, peptide vesicles have been developed for drug delivery methods. As used herein, the term "peptide vesicle" includes small membrane enclosed sacs, usually containing liquid or gas, formed from block copolymers or block copolypeptides (when amino acids are used) and is used interchangeably with polymersomes, polymer vesicles, peptosomes, and oligo- or polypeptide vesicles.

Existing methodologies for preparing peptide vesicles include the use of various diblock or triblock copolymers, where blocks of hydrophobic and hydrophilic amino acids (in their natural or modified forms) are linearly copolymerized. Block copolymer amphiphiles are polymers that are composed of segments of repeating units covalently linked together wherein the segments can have different properties to give the polymer an amphiphilic nature. The ability of diblock copolymers to possess both a hydrophobic and hydrophilic block gives these polymers a lipid-like character, yet with greater stability than their lipid counterparts. These blocks in block copolymers can be synthetic, semisynthetic or, as recently shown, composed entirely of biological building blocks like amino acids. Amino acid block copolymers can range anywhere from 30aa to 120aa or more, and like other block copolymers are capable of self-assembling into micelles, vesicles, bilayers or other ordered structures. These assemblies require the peptides to adopt a helical structure in their final assembled structure. Existing reported structures have been generated from linear block polypeptides and have characteristics similar to lipids.

More recently, polypeptide vesicles have been formed from copolypeptides of the type $K_xL_y$, $E_xL_y$ and $R_xL_y$, where K is lysine, L is leucine, E is glutamic acid, and R is arginine, and where x can range up to 60 units and y up to 20 units. These copolypeptides have been shown to form various structures including micelles, vesicles and vesicle-inside-vesicles. They have shown that in general, the shape and size of the structures formed can be controlled by varying the hydrophobicity or the overall chain length of the polypeptide. Others have tried synthesizing copolymers/copolypeptides to develop vesicles that can act as biomimetic encapsulants. Examples include: poly (styrene)-b-poly(acrylamide); poly (styrene)-b-poly(isocyanide) copolymers; EO40-EE37(polyethylene oxide-polyethylenethylene); PB40-b-PGA100 poly (butadiene)-b-poly(γ-L-glutamic acid); glycine based peptides (G4D2, G6D2, G8D2, G10D2); $K_{100}L_{20}$; $K_{60}L_{20}$; H-Glu-ΔPhe-OH and H-Lys-ΔPhe-OH Amphiphilic dipeptides; and poly (sarcosine)-poly(γ-L-glutamic acid).

Although, it is usually considered that polymersomes formed from block copolymers are high in molecular weight (MW>>10 kDa), the simplest unit so far mentioned in literature involved in the formation of vesicles that can act as a encapsulant is a dipeptide.

SUMMARY OF THE INVENTION

The invention provides branched, amphipathic peptides comprising a hydrophilic component, a branch point, and two respective hydrophobic components. The peptides are selected from the group consisting of bis(h)-K-$K_n$ and the N-acetylated derivatives thereof, where -K- is a branched lysine residue, K is lysine, h is a hydrophobic amino acid sequence selected from the group consisting of FLIVIGSII (SEQ ID NO: 3), FLIVI (SEQ ID NO: 4), and VFFIVIL (SEQ ID NO: 5), and n is from about 1 to about 7.

The present invention also provides an aqueous composition comprising a plurality of a first amphipathic, branched peptide and a plurality of a second amphipathic, branched peptide, wherein the first and second peptides each comprise a respective hydrophilic component, a branch point, and two respective hydrophobic components. The first and second peptides are preferably different. That is, the first peptide has a first number of amino acid residues, and the second peptide has a second number of amino acid residues, wherein the first number of amino acid residues is different from the second number of amino acid residues.

The invention is also concerned with a dried composition comprising a plurality of a first amphipathic, branched peptide and a plurality of a second amphipathic, ranched peptide, wherein the first and second peptides each comprise a respective hydrophilic component, a branch point, and two respective hydrophobic components. The first peptide also has a first number of amino acid residues, and the second peptide has a second number of amino acid residues, wherein the first number of amino acid residues is different from the second number of amino acid residues. The dried composition also comprises less than about 10% by weight moisture, based upon the total weight of the composition taken as 100% by weight, A peptide vesicle is also provided. The vesicle comprises a Waver membrane having interior and exterior layers and defining a liquid receiving interior space. The membrane comprises a plurality of a first amphipathic, branched peptide having a first number of amino acid residues, and a plurality of a second amphipathic, branched peptide having a second number of amino acid residues, wherein the first and second peptides are different. That is, the first number of amino acid residues in the first peptide is different from the second number of amino acid residues in the second peptide. The first and second peptides also each comprise a respective hydrophilic component, a branch point, and two respective hydrophobic components.

The invention is also concerned with a method of forming a peptide vesicle. The method comprises dispersing or dissolving a plurality of a first amphipathic, branched peptide having a first number of amino acid residues in an aqueous solvent to form a first aqueous dispersion or solution. A plurality of a second amphipathic, branched peptide is also dispersed or dissolved in an aqueous solvent to form a second aqueous dispersion or solution, wherein the second peptide has a second number of amino acid residues different from the first number of amino acid residues. The first and second peptides also each comprise a respective hydrophilic component, a branch point, and two respective hydrophobic components. In the method, the first and second aqueous dispersions or solutions are mixed to form a heterogeneous dispersion or solution of peptides. The solvent is removed to form a dried mixture of peptides, and the dried mixture of peptides is rehydrated with water to form a vesicle formation solution comprising a heterogeneous mixture of the first and second peptides. Advantageously, the vesicles are spontaneously formed in the vesicle formation solution without further treatment (i.e., sonication or extrusion).

The invention also provides a pharmaceutically acceptable composition comprising a plurality of peptide vesicles, as described herein, and an active agent encapsulated in the vesicle.

A method of targeting delivery of an active agent to a region of a patient is also provided. The method comprises administering to a patient a peptide vesicle, as described herein, which encapsulates the active agent. Advantageously, the vesicle further comprises a targeting moiety on the exterior surface of said membrane for automatic selective uptake by the targeted tissue or region of interest.

The invention is also concerned with a method of encapsulating an active agent. The method comprises dispersing or dissolving the active agent and a mixture of a plurality of a first amphipathic, branched peptide and a plurality of a second amphipathic, branched peptide in an aqueous solution, and allowing the dispersion or solution to stand for at least 2 hours to thereby form vesicles. The vesicles have a bilayer membrane encapsulating the active agent. The first and second peptides used to form the vesicles are preferably different. That is, the first peptide has a first number of amino acid residues, and the second peptide has a second number of amino acid residues, wherein the first number of amino acid residues is different from the second number of amino acid residues. In addition, the first and second peptides each comprise a respective hydrophilic component, a branch point, and two respective hydrophobic components.

BRIEF DESCRIPTION OF THE DRAWINGS

FIG. 1 illustrates the two preferred branched, amphipathic peptides bis($h_9$)-K-$K_4$ and bis($h_5$)-K-$K_4$ synthesized in Example 1, and a third branched, amphipathic peptide bis($h_7$)-K-$K_4$ in accordance with the invention;

DETAILED DESCRIPTION OF THE INVENTION

Figure 2:
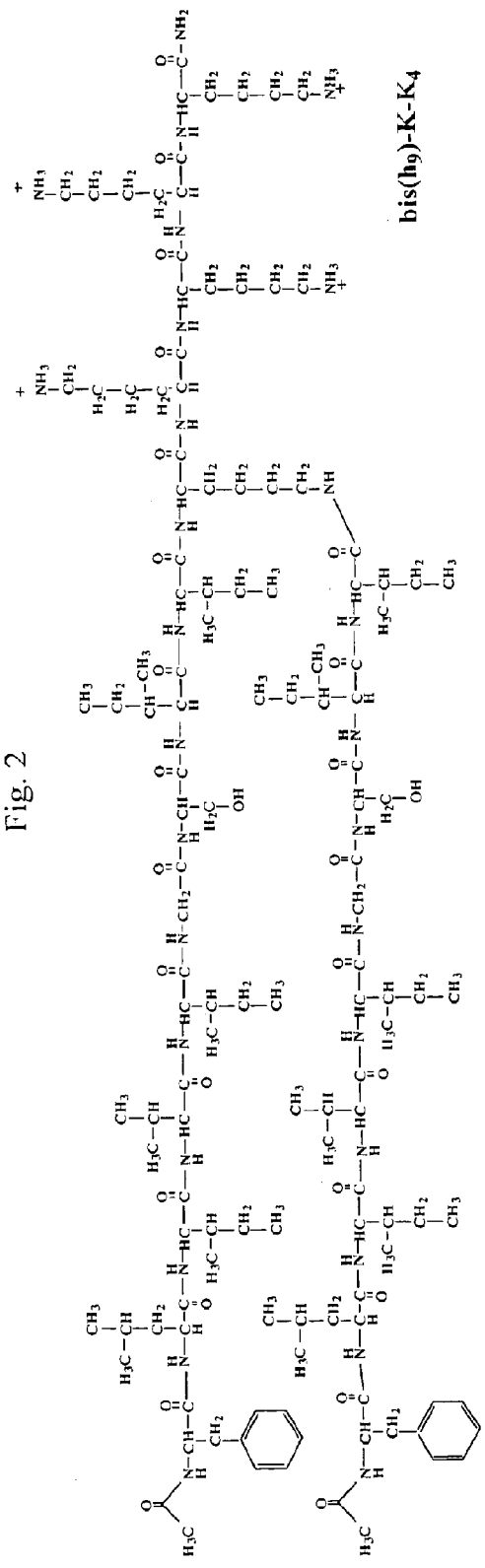
FIG. 2 illustrates two preferred branched, amphipathic N-acetyl-capped peptides bis($h_9$)-K-$K_4$ and bis($h_5$)-K-$K_4$ synthesized in Example 1.
Figure 2:
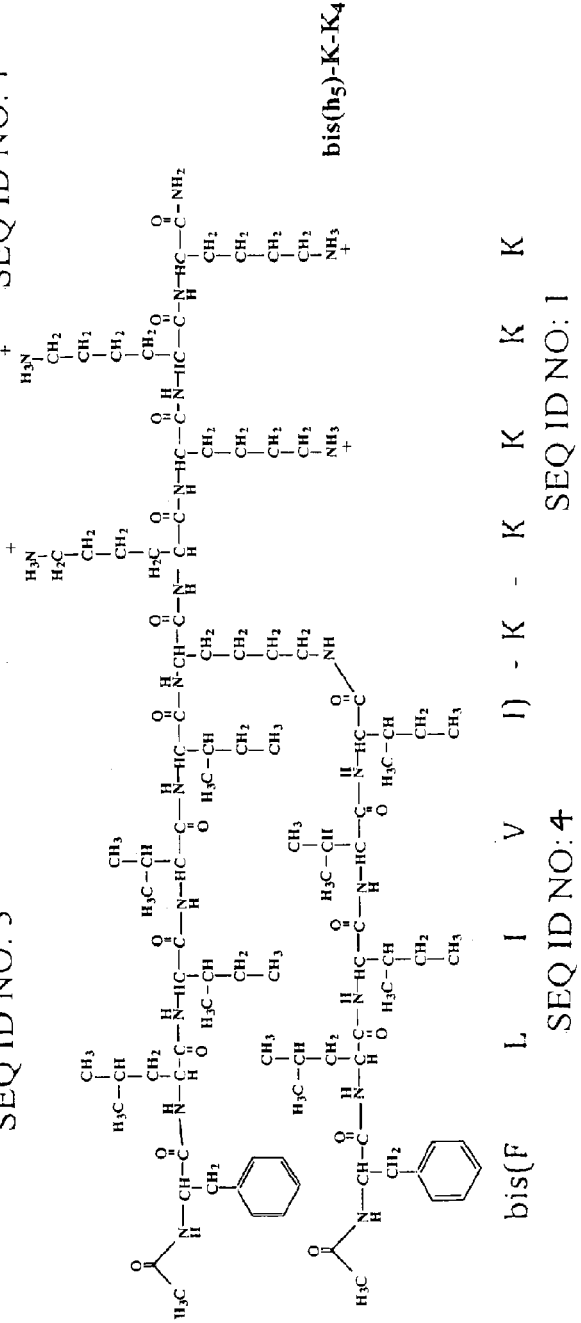

In more detail, the present invention provides novel peptide vesicles that can be used to encapsulate active agents. The vesicles are substantially spherical-shaped, aggregates of peptides, which define the vesicle membrane and enclose fluid comprising the active agents in the interior space (i.e., hollow core of the vesicle). Active agents that can be encapsulated in the vesicles include among other things, drugs and other therapeutic molecules, bioactive compounds, enzymes and other proteins and peptides, and DNA and RNA fragments. Excipients and other carriers or solutions may also be included inside the vesicles. The vesicles provide a protective shell that shields the active agent from the external environment, which could prematurely inactivate the active agent. As drug delivery vehicles, the novel vesicles can also be used to alter the biological half-life of an active agent, thus making it time-released.

The vesicle membrane is comprised of amphiphilic block copolymers, and creates a physical barrier substantially isolating the encapsulated material from the external environment. The membrane can be permeable, non-permeable, or semi-permeable, and is preferably semi-permeable. The vesicle membrane preferably comprises a bilayer morphology similar to liposomes. More preferably, the vesicle membrane consists (or consists essentially) of a bilayer of interlocking peptides. That is, the vesicle membrane is preferably substantially free of lipids or phospholipids. The bilayer is preferably heterogeneous, comprising at least two different peptides, preferably having different chain lengths. Unlike existing linear peptide diblock copolymers, the inventive copolymers used in forming the peptide vesicles of the present invention preferably comprise branched (, non-linear) peptide sequences. The peptides can either be of the all L-stereo configuration or D-stereo configuration. Preferably, the peptides are amphipathic and comprise an oligo-lysine (K=n) C-terminus with the alpha-and epsilon-amino groups of the N-terminal lysine acting as the branch points for two hydrophobic beta-sheet forming sequences. The resulting peptides, in their broadest terms, have a hydrophilic (polar) component, a branch point, and two hydrophobic components. Thus, the hydrophobic components of the peptides are each preferably coupled to the same amino acid residue which serves as the branch point attached to the hydrophilic component, resulting in a hydrophilic "head" and two hydrophobic "tails," similar to the morphology of a class of lipids called diacylphospholipids. The term "beta-sheet" conformation or structure, as used herein, refers to secondary protein structure where the protein forms overlapping layers, thus forming a beta-pleated sheet. Such beta-pleated sheets may reside in either a "parallel orientation"(i.e., the N-termini of successive strands are oriented in same direction), or in "anti-parallel orientation"(, the N-terminus of one strand is adjacent to the C-terminus of the next).

The hydrophilic (polar) lysine sequences are preferably from about 1 to about 7 lysine residues in length, more preferably from about 1 to about 6 lysine residues, and even more preferably from about 1 to about 5 lysine residues. A particularly preferred lysine sequence is KKKK (SEQ ID NO: 1). The lysines can have a net positive charge at physiological pH values (7.2-7.4). A further uncharged N-terminal lysine residue is provided in the peptide as the branch point (-K-).

The branched hydrophobic sequences (or tails) are preferably each from about 3 residues to about 11 residues in length, and more preferably from about 4 to about 10 residues in length, and even more preferably from about 5 to about 9 residues in length. The hydrophobic tails are preferably isolated from an internal fragment of the human dihydropyridine-sensitive L-type calcium channel segment CaIVS3 (DP-WNVFDFLIVIGSIIDVILSE; SEQ ID NO: 2). In the CaIVS3 context, the peptide is part of a transmembrane helix that forms the central water-lined pore of a calcium channel. The hydrophobic components of the peptide are preferably selected from the group consisting of FLIVIGSII ("$h_9$;" SEQ ID NO: 3), FLIVI ("$h_5$;" SEQ ID NO: 4), and VFFIVIL ("$h_7$;"SEQ ID NO: 5). SEQ ID NO: 5 is a novel sequence loosely based on the CaIVS3 hydrophobic segment. In the new primary structural context all these branched sequences adopt a beta-sheet structure. In some embodiments, the N-terminal end of each hydrophobic tail can be capped with all acetyl group.

It is particularly preferred that the peptides used to form the vesicles are selected from the group consisting of bis(h)-K-$K_n$, where h is a hydrophobic amino acid sequence selected from the group consisting of FLIVIGSII ("$h_9$;" SEQ ID NO: 3), FLIVI ("$h_5$;" SEQ ID NO: 4), and VFFIVIL ("$h_7$;"SEQ ID NO: 5), -K- is a branched lysine residue, K is a hydrophilic lysine residue, and n is from about 1 to about 7 (preferably from about 1 to about 6, and more preferably from about 1 to about 5), Three exemplary peptides are shown in FIG. 1. As noted above, the N-terminal end of each h sequence can be capped with an acetyl group (Ac). See FIG. 2. The peptides preferably have a molecular weight ranging from about 781 Da to about 3345 Da, and more preferably from about 1116 Da to about 2999 Da, and even more preferably from about 1675 Da to about 2653 Da. The "molecular weight" for these peptides is an average weight calculated based upon the total MW of the actual amino acids present divided by the # of residues. The peptides preferably have an overall chain length ranging from about 7 amino acid residues to about 29 amino acid residues, more preferably from about 10 residues to about 26 residues, and even more preferably from about 15 residues to about 23 residues. Particularly preferred peptides are selected from the group consisting of bis($h_9$)-K-$K_4$, bis($h_5$)-K-$K_4$, and N-acetylated derivatives thereof. More preferably, the bilayer vesicle membrane consists (or consists essentially) of alternating and interlocking sequences bis($h_9$)-K-$K_4$ and bis($h_5$)-K-$K_4$, or the N-acetylated derivatives thereof.

The method of forming the peptide vesicles comprises mixing a first peptide and a second peptide together. Specifically, the method comprises dissolving or dispersing a plurality of the first peptide and a plurality of the second peptide in an aqueous solution to form a heterogenous dispersion or solution of peptides, wherein the first peptide and second peptide are preferably different (i.e., have different chain lengths). More preferably, the first peptide and second peptide are first dissolved or dispersed in an aqueous solvent to form respective aqueous solutions, which are then mixed together. Suitable aqueous solvents are selected from the group consisting of 2,2,2-trifluoroethanol (TFE), tetrahydrofuran (THF), and acetonitrile, in water, with IFE being particularly preferred. In one aspect, the individual peptide solutions are prepared using an aqueous solvent comprising from about 20% v/v to about 80% v/v, and even more preferably about, 40% y/y TFE. The peptides themselves can be synthesized using any suitable method, such as the 9-fluorenylmethoxycarbonyl (Fmoc) strategy using Fmoc-protected amino acids as described herein, followed by lyophilization until use. The peptides in their individual solutions will preferably be observed to adopt a helical conformation, which can be confirmed by circular dichroism (CD) spectroscopy. The concentration of each peptide in their respective solutions will vary, but preferably ranges from about 0.001 mM to about 10 mM, more preferably from about 0.025 mM to about 7.5 mM, and even more preferably from about 1 mM to about 5 mM. The first peptide and second peptide are then preferably mixed at a molar ratio of from about 1:10 to about 10:1, more preferably from about 1:5 to about 5:1, and most preferably at about 1:1. The concentration of the first peptide in the combined solution preferably ranges from about 0.001 mM to about 10 mM, more preferably from about 0.01 mM to about 5 mM, and even more preferably from about 0.025 mM to about 2 mM. The concentration of the second peptide in the combined solution preferably ranges from about 0.001 mM to about 10 mM, more preferably from about 0.01 mM to about 5 mM, and even more preferably from about 0.025 mM to about 2 mM. The total concentration of the peptides in the solution will vary, but preferably ranges from about 0.001 mM to about 10 mM, more preferably from about 0.01 mM to about 5 mM, and even more preferably from about 0.025 mM to about 2 mM.

Regardless of the embodiment, once mixed, the solvent is then removed, preferably under vacuum, to produce a dried mixture comprising, and preferably consisting of, the first and second peptides. The dried mixture preferably comprises less than about 10% by weight moisture, and more preferably less than about 5% by weight moisture, based upon the total weight of the dried mixture taken as 100% by weight. Put another way, the first and second peptides preferably comprise about 90% by weight of the dried mixture, and more preferably about 95% by weight of the dried mixture, based upon the total weight of the dried mixture taken as 100% by weight.

Once the solvent is removed, the dried peptide mixture is then rehydrated with water (preferably via dropwise addition) until the final desired concentration of each peptide dissolved in water is reached to form a vesicle formation solution comprising a heterogeneous mixture of the first and second peptides. The concentration of the first peptide in the vesicle formation solution preferably ranges from about 0.001 mM to about 10 mM, more preferably from about 0.01 mM to about 5 mM, and even more preferably from about 0.025 mM to about 2 mM, The concentration of the second peptide in the vesicle formation solution preferably ranges from about 0.001 mM to about 10 mM, more preferably from about 0.01 mM to about 5 mM, and even more preferably from about 0.025 mM to about 2 mM. The total concentration of the peptides in the vesicle formation solution will vary, but preferably ranges from about 0.001 mM to about 10 mM, more preferably from about 0.01 mM to about 5 mM, and even more preferably from about 0.025 mM to about 2 mM. Preferably, the peptides are rehydrated using distilled deionized (DDI) water. Material to be encapsulated in the vesicles is added during the rehydration step, and can be added separately or in a solution with the water used to rehydrate the dried peptide mixture. The pH of the solution is also preferably adjusted using a dilute solution of NaOH (0.005% w/v), and ranges from about 4 to about 9, more preferably from about 5.5 to about 8.5, and even more preferably from about 6 to about 8. The vesicle formation solution is then allowed to stand under ambient conditions at room temperature (~25° C.) for at least about 0.05 hours, more preferably from about 1 to about 3 hours, and even more preferably from about 1.5 to about 2 hours.

Figure 3:
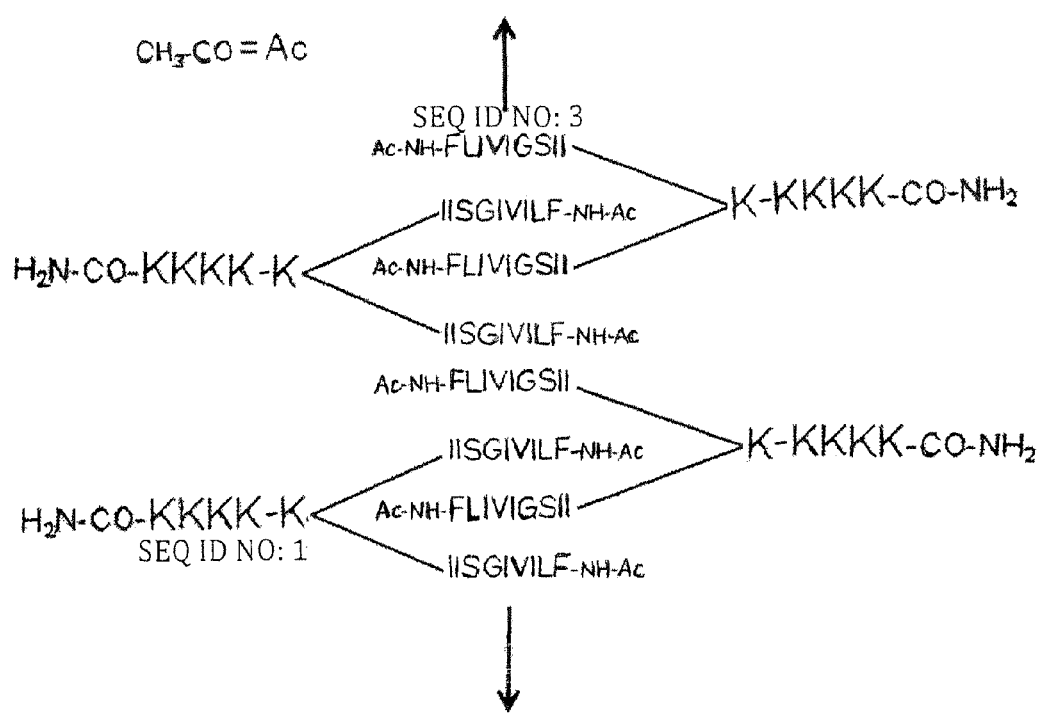
FIG. 3 depicts a homo-assembly of bis($h_9$)-K-$K_4$ peptides in a vesicle membrane bilayer to illustrate the hypothetical anti-parallel packing of the hydrophobic tails.

Unlike existing peptide vesicles, which adopt a helical secondary structure, the inventive peptides will preferably be observed to adopt a beta-sheet secondary structure in vesicle formation. That is, the hydrophobic segments of the peptides are unique in that they have a strong propensity to form beta-sheet structures in water. More preferably the first and second peptides form a unique interlocking bilayer arrangement which forms the vesicle membrane. Advantageously, the peptides spontaneously (or automatically) self-assemble into nano- or micro-vesicles when dissolved in water without the need for any additional treatments such as sonication or extrusion (as is required by existing methods of forming liposomes), or post-assembly polymerization or crosslinking. As shown in FIG. 3, the bilayer comprises an exterior and an interior layer. The hydrophobic residues face inward defining the inner "core" of the vesicle membrane, while the positively charged lysines face outward from the core of the membrane towards the internal and external vesicle environments and thereby define the interior and exterior surfaces of the membrane. The shorter peptides will preferably predominately occupy the inner layer of the assembled peptide bilayer, while larger peptides will preferably predominately occupy the outer layer of the bilayer. The first and second peptides associate in a type of hydrogen-bond-stabilized anti-parallel beta-sheet structure, which is unique to the inventive peptide bilayer. More specifically, the respective hydrophobic tails of the first and second peptides interdigitate, and the beta-sheets formed have an anti-parallel orientation, in which the opposed sequences interlock to form a zipper-like structure in three dimensions (see FIG. 3). The resulting bilayer forms the vesicle membrane in a substantially spherical shape which defines the liquid-receiving interior space (cavity) of the vesicle. Rather than relying on weak hydrophobic interactions that stabilize traditional. lipid bilayers, these inventive assemblies utilize hydrogen bonds between adjacent sequences. The hydrogen bonds are considerably stronger and help keep the peptide assembly together at reduced concentrations where lipid vesicles would breakdown.

Preferably, after two hours of mixing, the vesicles are less than about 250 nm in diameter, more preferably from about 25 nm to about 250 nm in diameter, and even more preferably from about 50 nm to about 200 nm in diameter. Larger vesicles can be formed by neutralizing the net positive charge of the exterior lysine residues; thereby allowing the formerly surface-charged vesicles to come closer together and fuse into larger structures. Upon standing for about 48 hours in the presence of a suitable neutralizer, such as 5,6-carboxyfluorescein, the vesicles fuse giving rise to larger structures with diameters greater than about 1 μm, preferably from about 2 μm to about 12 μm, and more preferably from about 5 μm to about 10 μm. After standing for about 72 hours in the presence of a neutralizer, the vesicles preferably have diameters greater than about 50 μm, more preferably from about 10 μm to about 100 μm, and even more preferably from about 20 μm to about 40 μm. In one aspect, the vesicle size can be stabilized by treatment with dilute glutaraldehyde to introduce limited crosslinks between adjacent lysines on the outside of the vesicle.

Advantageously, the vesicles can be prepared for targeting of specific cell surface receptors through adduction of the C-terminal lysine with different molecules or functional groups, such as cholesterol, mannose, TAT peptide, insulin, biotin, nucleotides, or any other suitable known surface targeting molecules, and combinations thereof. The vesicles having such targeting moieties conjugated to the vesicle membrane exterior surface will therefore localize in and be selectively taken up by specific cells or tissues of a patient. Thus, the vesicles can be used for targeted therapies (gene therapy, cancer treatment, etc.), and nanodrug delivery by administering the vesicles having the targeting moieties to a patient. The targeting moiety is attached to the hydrophilic components of the peptides used to form the vesicle membrane. More preferably, the targeting moiety is attached to the hydrophilic component of the larger of the two peptides, which will preferably predominately occupy the outer layer of the bilayer membrane, thus presenting the targeting moiety on the exterior surface of the vesicle after formation. The moiety will be recognized by the targeted region or tissue in the patient, and the vesicles will automatically localize in that region or tissue.

The vesicles can also be made invisible to the immune system by incorporating just D-amino acids into the vesicle forming peptides. Certain pH, protease, or nuclease sensitive drugs can also be made orally active using the inventive vesicles. That is, the protective shell would allow such drugs to pass through various parts of the GI tract where inactivating molecules exist. Suitable active agents for encapsulating in the inventive vesicles, with or without excipients, include those selected from the group consisting of therapeutic molecules (e.g., small molecule drugs, larger molecular weight drugs (i.e., greater than about 125 Da)), radioactive isotopes, RNA oligomers, quantum dots, DNA plasmids, enzymes, poisons, toxins, secondary messengers, dyes, and combinations thereof. The vesicles can be used in pharmaceutically acceptable compositions for delivering the active agents and can be administered orally, intravenously, subcutaneously, intramuscularly, nasally, intraocularly, or aerosolized to a patient. It will be appreciated that the vesicle concentration in the composition will depend upon the active agent being delivered, but the concentration of vesicles will preferably range from about 0.001 mM to about 10 mM, more preferably from about 0.01 mM to about 5 mM, and even more preferably from about 0.025 mM to about 2 mM.

EXAMPLES

The following examples set forth methods in accordance with the invention. It is to be understood, however, that these examples are provided by way of illustration and nothing therein should be taken as a limitation upon the overall scope of the invention.

Example 1

Peptide Synthesis

1. Uncapped Peptides

In this procedure, branched peptides are synthesized using traditional solid phase chemistry and 9-fluorenylmethoxycarbonyl (Fmoc)-protected amino acids on CLEAR-amide resin on a model No. 431 peptide synthesizer (Applied Biosystems; Foster City, Calif.). This resin blocks the C-terminus with a carboxyamide moiety. The synthesis of the peptide begins with the first amino acid, lysine (with its α-amino group blocked with Fmoc and its ε-amine group blocked with t-Boc) attached covalently to the resin. The t-Boc at the ε-amine group allows for linear extension of the peptide while preventing any side reactions at the side-chain amino group. Three more lysines are added in a likewise fashion to produce the tetra-lysine C-terminal segment. After the fourth Fmoc/t-Boc lysine is attached, a fifth lysine with both the α- and ε-amine groups blocked with Fmoc groups [$Na^{\alpha,\epsilon}$ di-Fmoc-L-Lysine] $C_{36}H_{34}N_2O_6$, is added. This special amino acid allows for the introduction of a single branch point. The subsequent release of the two Fmoc protecting groups allows for the simultaneous addition of two identical amino acids to the bifurcated chain. Now, upon the addition of new Fmoc-protected amino acids, extension occurs at both sites, thereby permitting the synthesis of the bis-hydrophobic tails attached to the common C-terminal oligo-lysine branch point: FLIV-IGSII ($h_9$;SEQ ID NO; 3) or FLIVI ($h_5$; SEQ ID NO: 4). The stepwise addition of amino acids to both the α- and ε-amine of a lysine was previously described by Iwamoto et al. 1994 Int. J. Peptide Protein Res. Vol. 43, pages 597-607. The resulting branched peptide sequences are shown in FIG. 1.

The peptides, after double-chain extension of the hydrophobic tails, are cleaved with simultaneous deprotection by treatment with water in 95% trifluoroacetic acid for 2 hours at room temperature. The cleaved peptides are then washed four times with diethyl ether and dissolved in DDI water, and then lyophilized. Peptides of the all L- or all D-stereo configuration will work as long as the two types are not mixed. All D-amino acid sequences may prove useful in preventing undesirable immune or inflammatory responses.

2. N-acetyl Capped Peptides

Peptides with their N-termini capped with an acetyl group as the final step on the synthesizer were done so as to remove the charges on the N-termini ends. In the above procedure, the peptides, after double-chain extension of the hydrophobic tails, are capped with acetic anhydride in NMP containing N,N-Diisopropylethylamine for 20 mm. The peptides are subsequently cleaved, as above, with simultaneous deprotection by treatment with water in 95% trifluoroacetic acid for 2 hours at room temperature. The cleaved peptides are then washed four times with diethyl ether and dissolved in water, and then lyophilized. This synthesis was characterized by matrix assisted, laser desorption-ionization time-of-flight (MALDI-TOF) mass spectroscopy on an Ultraflex II instrument (Bruker Daltronics, Billerica, Mass.).

Example 2

Vesicle Preparation Using N-Acetyl Capped Peptides

In this Example, a general method of vesicle preparation will be described using N-acetyl capped peptides, although it will be appreciated that the same procedure could be carried out using uncapped peptides. Each of the N-acetyl capped lyophilized peptide samples prepared above is individually dissolved in DDI water and their absorbance read in a spectrophotometer. Peptide concentrations can be calculated using the molar extinction coefficient ($\epsilon$) of Phe in water at 257.5 nm (195 $cm^{-1}$ $M^{-1}$). The two peptides (bis($h_9$)-K-$K_4$ and bis($h_5$)-K-$K_4$) are then mixed together in an equimolar ratio and vortexed for a brief amount of time and allowed to stand for a few hours before removing the solvent under vacuum. In one experiment, the peptides were mixed to a final concentration of 1.6 mM of each peptide, followed by solvent removal. The dried samples are then redissolved in DDI water by dropwise addition. The rehydrated samples are then vortexed briefly and allowed to stand at least two hours before any measurements are made.

Circular Dichorism (CD) experiments, which actively monitor the intermolecular folding and intermolecular sheet assembly of peptide, provide a clear image of how the peptide properties can be attributed to molecule folding and consequent assembly mechanism. CD Spectroscopy was used to analyze the secondary structures formed by the individual peptides and the peptide mixture formed by the above process. All Spectra were collected in a Jasco J-815 CD spectrophotometer in a circular quartz cuvette with a pathlength of 0.1 mm at room temperature and measured in mdeg. Raw scans were processed (subtracted from blank and smoothed) using Spectra Analysis (registered software from Jasco).

Figure 4:
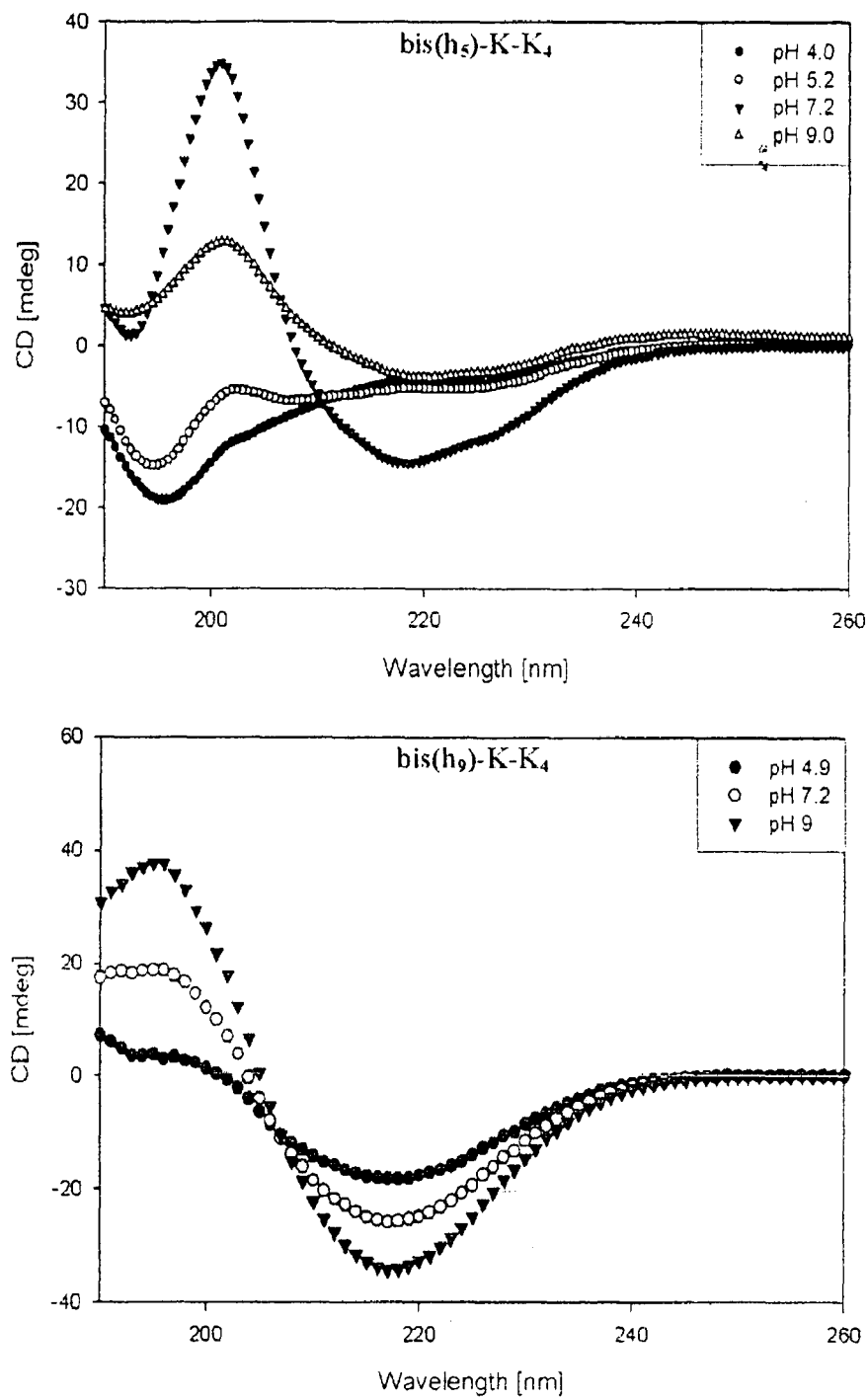
FIG. 4 are graph of the CD spectra for bis($h_9$)-K-$K_4$ alone, and bis($h_5$)-K-$K_4$ alone at the indicated pH values.
Figure 5:
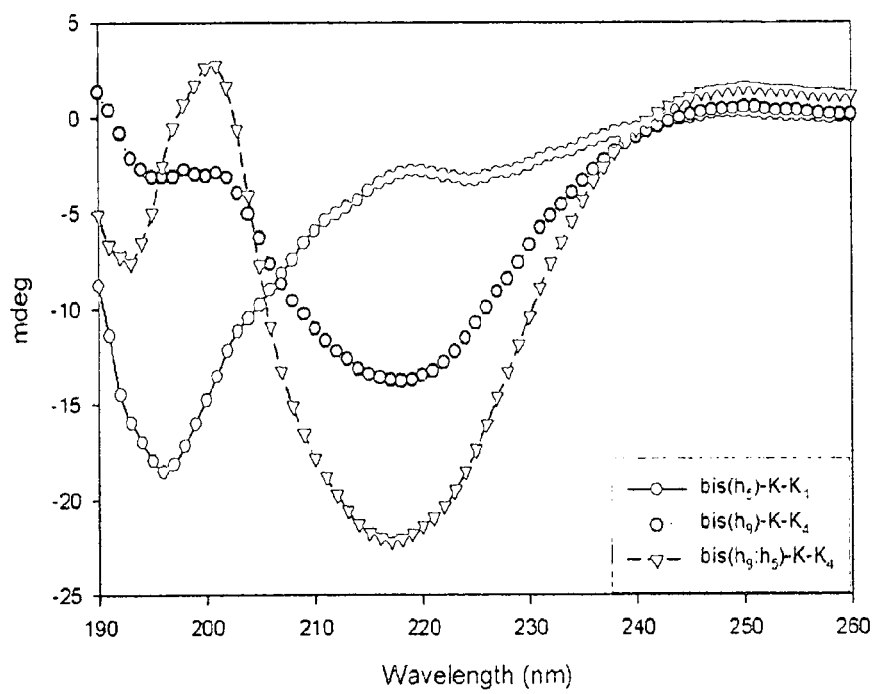
FIG. 5 is a graph of the CD spectra showing the effect of mixing bis($h_9$)-K-$K_4$ and bis($h_5$)-K-$K_4$ on β-sheet content at pH 4.

For the CD spectroscopy experiments, individual solutions of bis($h_9$)-K-$K_4$ alone, and bis($h_5$)-K-$K_4$ alone, were formed using DDI water each at a final peptide concentration of 1.6 mM, and a final volume of 500 μL. The individual solutions were analyzed at different pH levels, which were adjusted using a dilute solution of NaOH, and which are shown in the graph in FIG. 4. A mixture of the two peptides co-dissolved in DDI water at a 1:1 molar ratio was also formed at a concentration of 1.6 mM of each peptide, and a final volume of 500 μL. The pH was adjusted to 4.2 using a dilute solution of NaOH. From the results in can be seen that both sequence bis($h_9$)-K-$K_4$ and bis($h_5$)-K-$K_4$ are able to adopt a β-sheet conformation in aqueous buffers at neutral pH values (FIG. 4). The β-sheet content of bis($h_5$)-K-$K_4$ is considerably less than that seen for bis($h_9$)-K-$K_4$ and has a different pH profile. The peptide bis($h_5$)-K-$K_4$ shows maximal β-structure at neutral , while β-structure increases for bis($h_9$)-K-$K_4$ with increasing pH values over the ranges tested. Unexpectedly, when the two peptides are mixed the β-sheet content increases greater than the calculated sum of the peptides alone (see FIG. 5). The two sequences thus act synergistically to produce a complex that is higher in β-sheet content.

Example 3

Analysis of Uncapped Peptide Vesicles

In this Example, the vesicles prepared using uncapped peptides from Example 2 above were subjected to various analytical methods.

1. Transmission Electron Microscopy: Negative Staining

Figure 6:
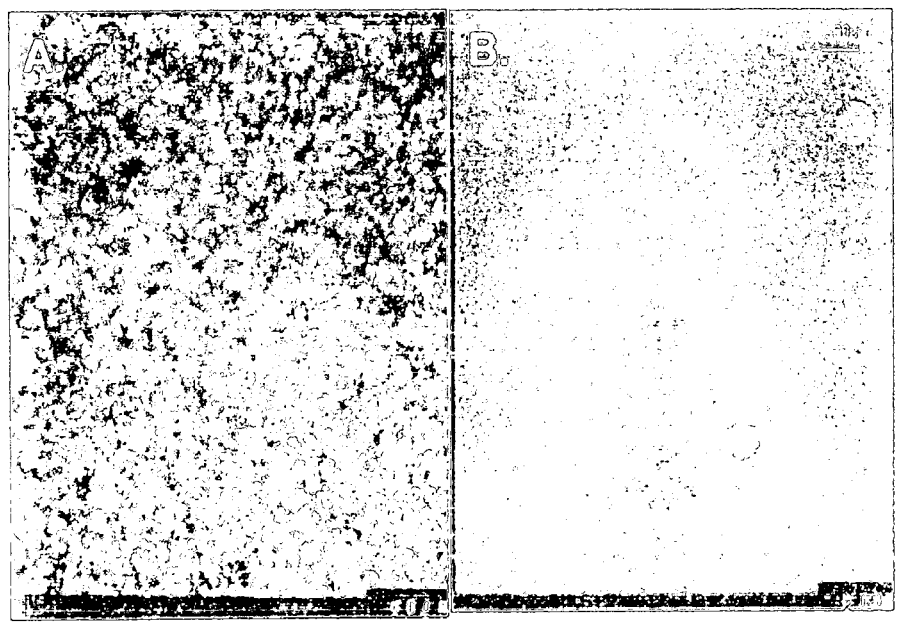
FIG. 6 depicts TEM images of a mixture of bis($h_9$)-K-$K_4$ and bis($h_5$)-K-$K_4$ peptides after 2 hours of incubation, showing: A. a sample of high density particles at 50K× magnification, stained with 10% phosphotungstic acid; and B. a dilute sample at 70K × magnification, stained using $OsO_4$ vapors.

In this procedure, the self-assembled vesicles were visualized using transmission electron microscopy (TEM). For phosphotungstic acid (PTA) staining, bis($h_9$)-K-$K_4$ was co-dissolved in DDI water at a 1:1 molar ratio with bis($h_5$)-K-$K_4$ for a final concentration of 1.6 mM of each peptide. Next, 15 μL of the peptide vesicle solution was placed on a copper grid (which in turn was placed on a piece of parafilm and placed in a petridish) and allowed to stand for 3 min. Excess peptide solution was wicked off using filter paper, followed by the addition of 15 μL of 10% PTA to the grid, which was allowed to stand for about 5 min. Excess PTA solution was wicked off using filter paper, and the grid was washed lightly with DDI water using a syringe. Excess water was wicked off and the grid was allowed to dry for at least 30 min. before TEM photos were taken (FIG. 6A.).

For osmium tetraoxide staining, bis($h_9$)-K-$K_4$ was co-dissolved in DDI water at a 1:1 molar ratio with bis($h_5$)-K-$K_4$ for a final concentration of 25 μM of each peptide. Next, 7 μL of the peptide vesicle solution was placed on a copper grid (which in turn was placed on a piece of parafilm and placed in a petridish) and allowed to stand for about 10 min. A drop of osmium tetroxide was placed a few inches away from the copper grid containing the peptide sample. The petridish was covered to allow the $OsO_4$ vapors to deposit on the peptide sample for a period of about 5 min. These grids were then allowed to dry for at least 15-20 min. before the TEM photos were taken (FIG. 6B.).

The vesicles, which are layered on top of each other, are on the order of 50 nm in diameter and appear fairly uniform in size.

2. Confocal Microscopy

Figure 7:
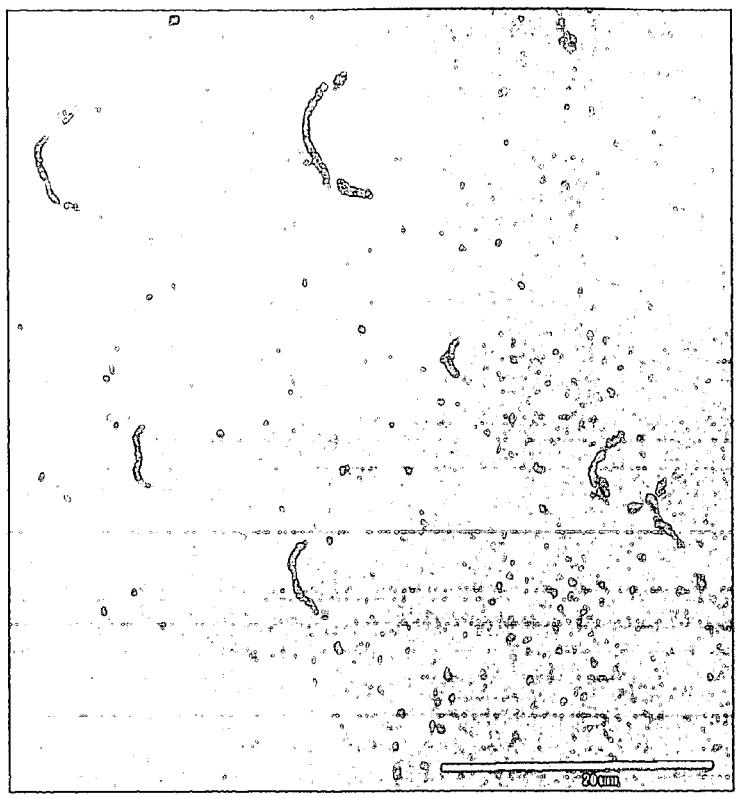
FIG. 7 is a confocal microscope image of a mixture of bis($h_9$)-K-$K_4$ and bis($h_5$)-K-$K_4$ at 100× magnification after 48 hours in the presence of 5,6-carboxyfluorescein, to aid in visualization.
Figure 8:
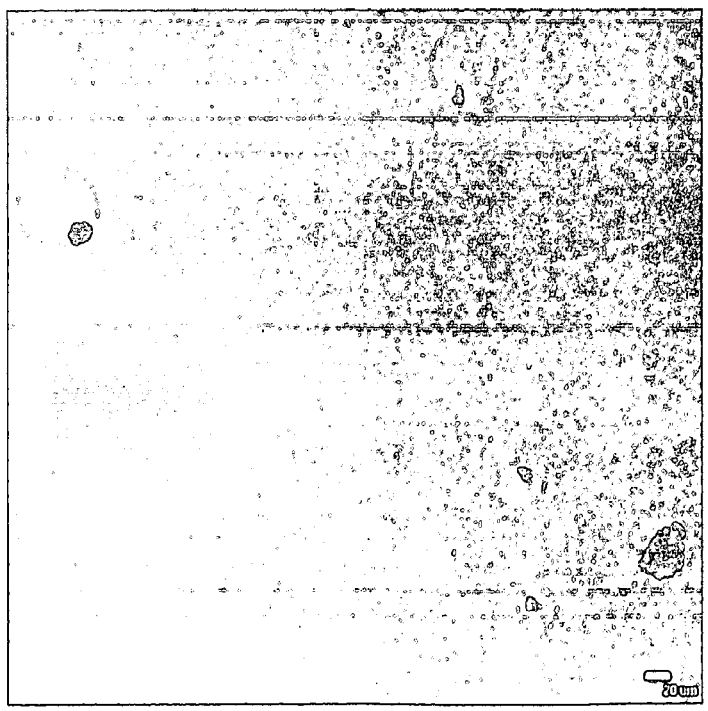
FIG. 8 is a confocal microscope image of a mixture of bis($h_9$)-K-$K_4$ and bis($h_5$)-K-$K_4$ at 20× magnification after 72 hours in the presence of 5,6-carboxyfluorescein, to aid in visualization.

Stock solutions of bis($h_9$)-K-$K_4$ and bis($h_5$)-K-$K_4$ in DDI water were co-dissolved at a 1:1 molar in a 5,6-carboxyfluorescein solution for a final peptide concentration of 1.6 mM each. About 25 μL of the sample was then mounted on a glass slide and covered with a coverslip and sealed. The slides were allowed to sit for 48-72 hours before pictures were taken using a confocal microscope. Upon sitting in the unbuffered 5,6-carboxyfluorescein solution for 48 hours, larger spherical entities than observed with TEM are formed, which can be seen with the light microscope. Specifically, in FIG. 7, peptides bis($h_5$)-K-$K_4$ and bis($h_9$)-K-$K_4$ at a 1:1 molar ratio when added to DDI water form larger vesicles on the order of 2-10 μm in diameter. In a separate experiment, the bis($h_9$)-K-$K_4$ and bis($h_5$)-K-$K_4$ peptides (1:1) when allowed to sit for three days (72 hours) in an unbuffered 5,6-carboxyfluorescein solution, formed even larger vesicles, exceeding 50 μm in diameter (see FIG. 8). The vesicles in this figure are large enough to have fluorescently-labeled peptide aggregates trapped within the vesicles.

Over time the small nano-vesicles are apparently able to combine through fusing to grow in size. The bis($h_5$)-K-$K_4$ sequence by itself is unable to form these structures. Although the bis($h_9$)-K-$K_4$ is able to form these vesicle-like structures, they are somewhat unstable and rapidly fuse to produce the larger structures.

From these timed experiments it is clear that nano-vesicles appear within 2 hours of mixing the peptides, and in time in the presence of 5,6-carboxyfluorescein (which serves to neutralize the net positive charge of the exterior lysine residues), fuse to form much larger structures that are as large or larger than human cells. As nano-vesicles, their size is on the order of adenovirus capsid particles, which have a diameter of 40-80 nm. The vesicles formed after 48 hours are on the order of human red blood cells, which have a diameter of 5-10 μm.

3. Sedimentation Analysis

The homogeneous peptide mixture was subjected to analytical ultracentrifugation for sedimentation analysis. A 1:1 molar ratio mixture of bis($h_5$)-K-$K_4$ and bis($h_9$)-K-$K_4$ was prepared at a final peptide concentration of 1.6 mM in DDI water. The pH was adjusted to 7.0 using a dilute solution of NaOH. For the analysis, 350 μL of each sample was loaded into a Beckman XL-I Analytical Ultracentrifuge cell and spun at 40,000 rpm for 3 hours at 20° C., with data collected using interference and absorbance optics. The raw data was then processed using DCDT+2.2.1 software to obtain g(s*) distribution. The results for the mixture showed a new molecular species in the range of 9.5-10.5 Svedberg units (S).

4. Isothermal Titration Calorimetry (ITC)

Based upon isothermal titration calorimetry, the Critical Assembly Concentration (CAC) for the individual peptides was determined to be less than 10 μM.

Example 4

Modified Vesicle Preparation Using N-Acetyl Capped Peptides

Figure 9:
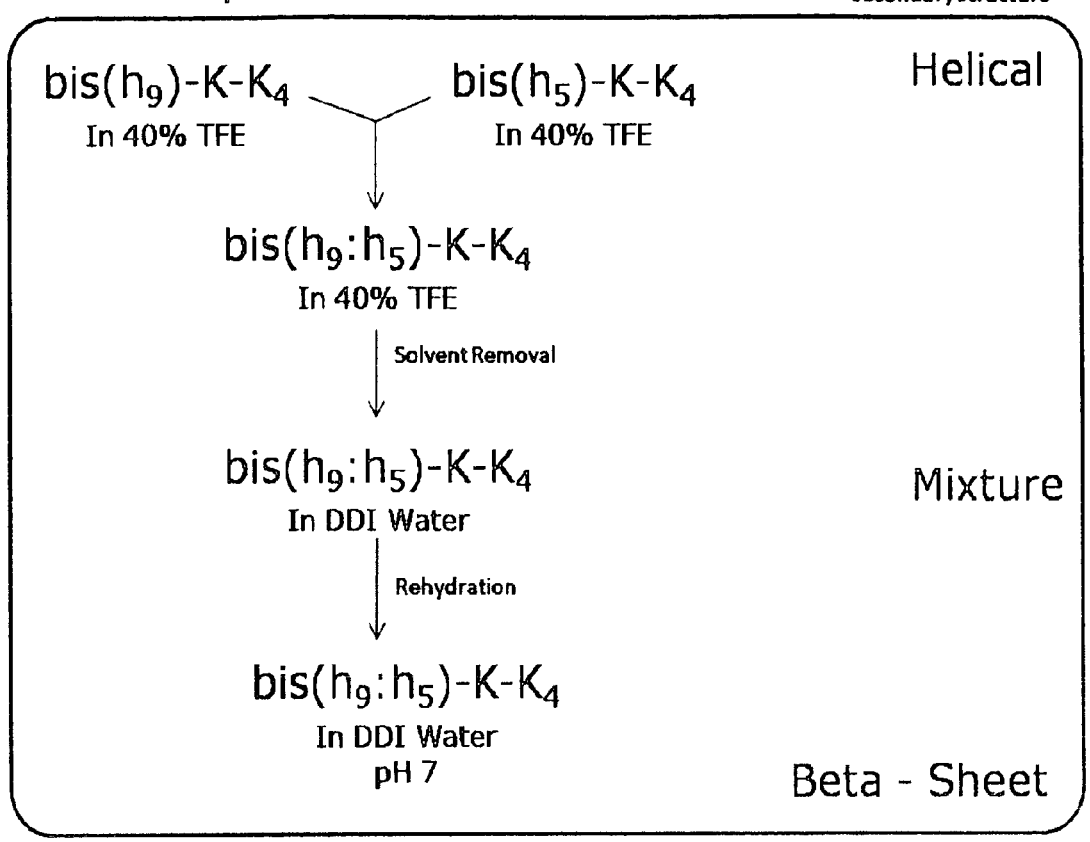
FIG. 9 is a flowchart showing a modified method of vesicle formation from Example 4.

In this Example, a modified procedure for preparing vesicles will be described using the N-acetyl capped bis($h_9$)-K-$K_4$ and bis($h_5$)-K-$K_4$ peptides synthesized in Example 1. It will be understood that this protocol can also be carried out using the uncapped peptides. A flowchart illustrating the procedure is provided in FIG. 9. The individual peptides are each initially dissolved in ~40% v/v TFE in DDI water in separate containers for a final peptide concentration of 3.0 mM each. The two peptide mixtures are then mixed at the desired ratio (e.g., 1:1 molar ratio) and concentration. Both peptides will be observed to adopt a helical conformation (as confirmed by CD Spectroscopy, see FIG. 10A.), which is believed to correspond to the monomeric state of the peptide.

Next, the solvent (~40% TFE in DDI water) is removed by placing the mixture in a speed vacuum for up to about 3 hours. Once the solvent is removed, the dry peptide mixture is then rehydrated by the dropwise addition of DDI water to the final desired concentration of each peptide. The pH of the sample is adjusted using a dilute solution of NaOH and the sample is allowed to stand for a couple of hours before any measurements are made.

Figure 10:
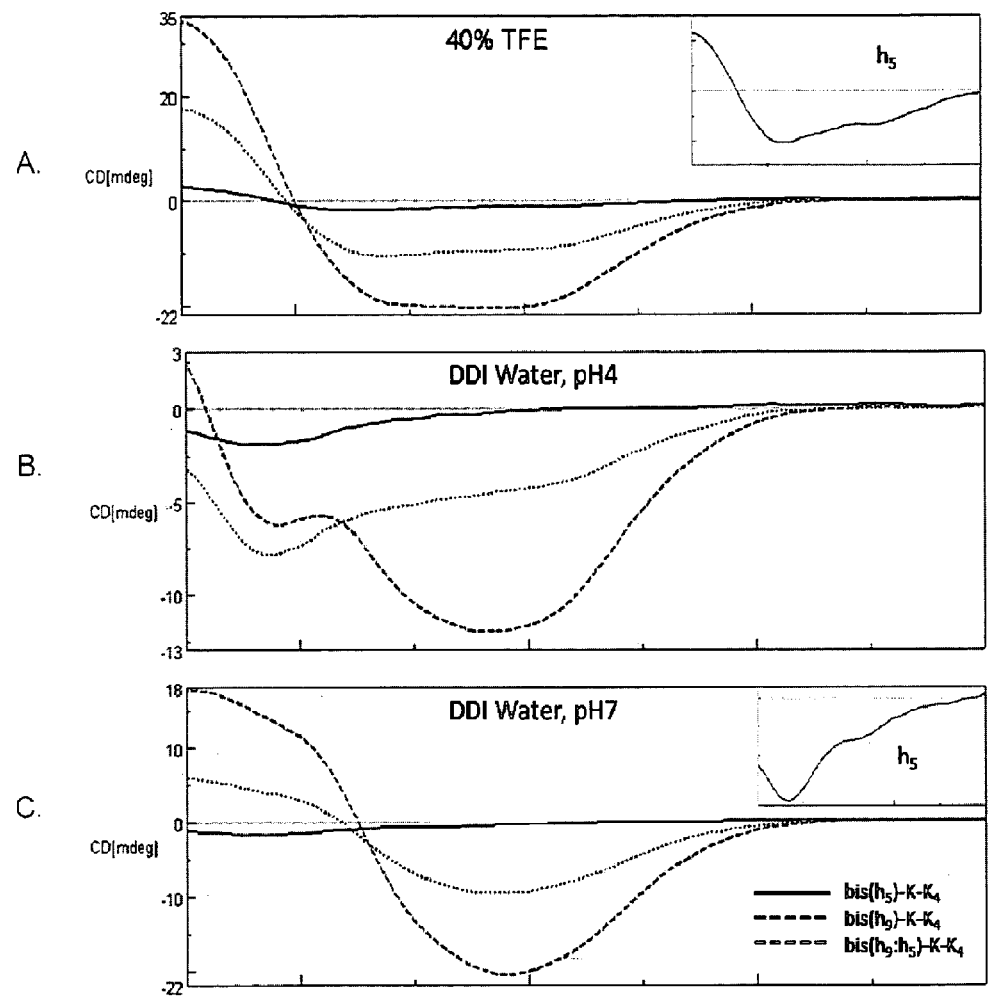
FIG. 10 is a graph of the CD spectra of bis($h_9$)-K-$K_4$ alone, bis($h_5$)-K-$K_4$ alone, and a mixture of the two peptides in: A. 40% 2,2,2-trifluoroethanol (TFE); B. DDI water at pH 4 after TFE removal; C. DDI water at pH 7 after TFE removal.

For example, CD spectra was collected of rehydrated solutions of bis($h_9$)-K-$K_4$ individually, bis($h_5$)-K-$K_4$ individually, and a 1:1 molar ratio of bis($h_9$)-K-$K_4$ and bis($h_5$)-K-$K_4$, each with a final peptide concentration of 1 mM. Two solutions were prepared for each sample, one at pH 4 (FIG. 10B.) and the other at pH 7 (FIG. 10C.). CD spectroscopy confirmed that the individual peptides and the peptide mixture in this final solvent condition (DDI water) adopted a β-sheet secondary structure. All spectra were collected using a Jasco J-815 CD spectrophotometer in a circular quartz cuvette with a path length of 0.1 mm at room temperature and measured in mdeg. Raw scans were processed (subtracted from blank and smoothed) using Spectra Analysis (registered software from Jasco).

The foregoing procedure could also be extended to include vortexing the final sample for 10 min. or more; temperature cycling by incubating the sample for 5 min. at 54° C. followed. by incubating for 5 min. at 4° C. and repeating this cycle at least 5-6 times; or sonicating the sample using ultrasound for anywhere between 5-15 min. to improve vesicle formation.

Other protocols to obtain peptide vesicles were attempted. Simple mixing of the individual peptides dissolved in acetonitrile (up to 90% v/v) in DDI water, or in 50% v/v tetrahydrofuran in DDI water did not form vesicles.

In earlier studies, FLIVIGSII (SEQ ID NO: 3) and FLIVI (SEQ ID NO: 4), when flanked by three lysine groups (i.e., KKKFLIVIGSIIKKK (SEQ ID NO: 6) and KKKFLIVIKKK. (SEQ ID NO: 7)), were observed to form nanofibrils made up of peptides arranged in β-sheets when dissolved at pH 12.0. These sequences displayed adhesive properties arising from the entanglement of the fibrils formed by β-structured peptides. Based on Fourier Transform Infrared Spectroscopy (FT-IR) and computer modeling studies, these peptides associate in an anti-parallel fashion to form the fibrils, which in turn become entangled. See U.S. Patent Application Pub. No. 2009/0105449, incorporated by reference herein. These sequences are unstructured at low and neutral pH and do not form vesicles. There is something quite special about the FLIVI(GSII) (SEQ ID NO: 3) sequence. Of a number of similar sequences from other sources including ones involved in Alzheimer's disease, the five-residue FLIVI (SEQ ID NO: 4) is the only sequence that will form β-sheet structures in water. All others show no structure in water. Both the all L- and all D-stereo configurations for the synthesized peptides can be used.

Example 5

Sedimentation Analysis

Figure 11:
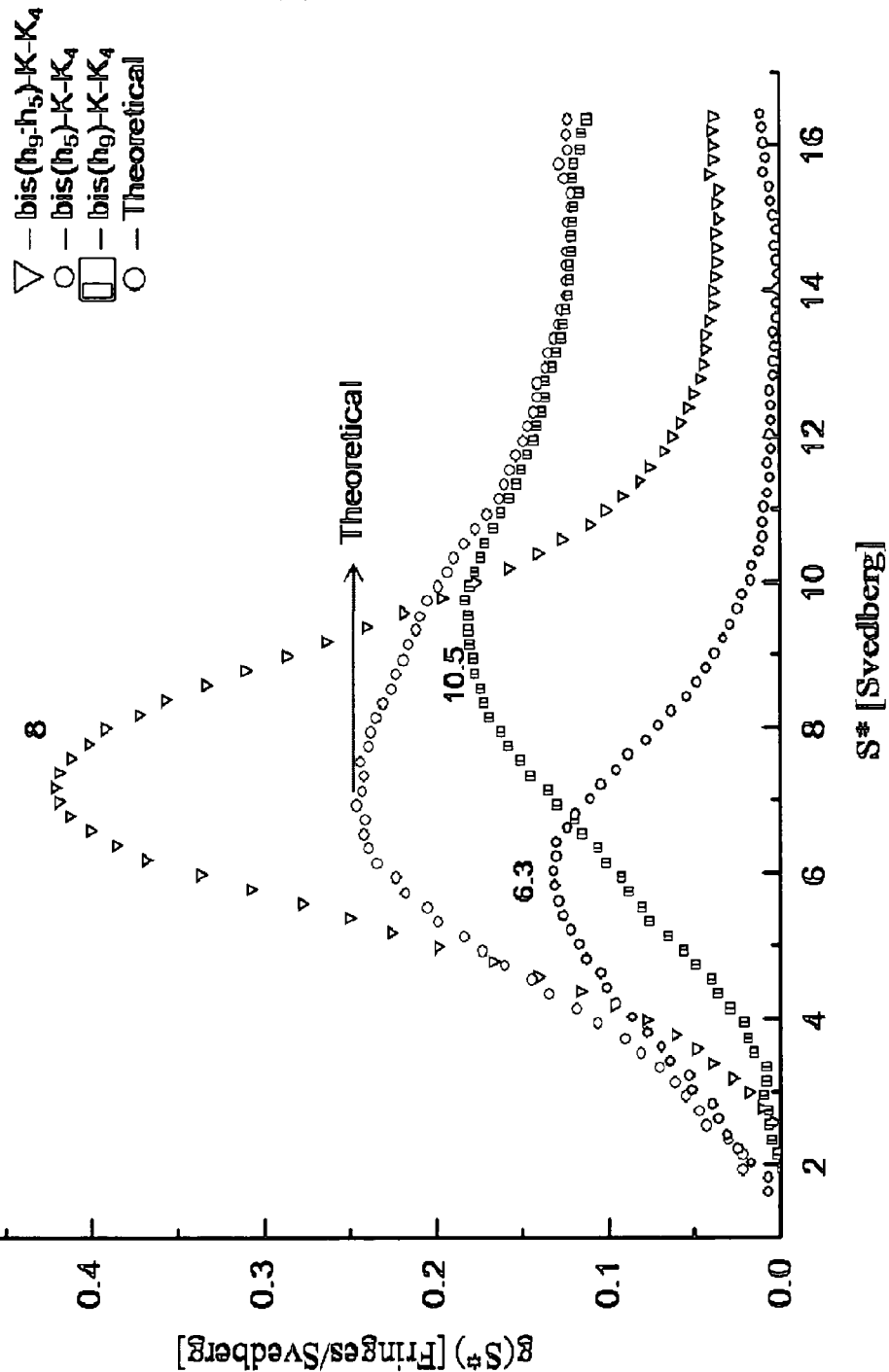
FIG. 11 is a graph showing peptide association as followed by sedimentation analysis from Example 5.

In this procedure, N-acetyl capped peptides were prepared using the protocol described in Example 1 above and subjected to analytical ultracentrifugation for sedimentation analysis. Three different samples were prepared from bis($h_5$)-K-$K_4$ alone, bis($h_9$)-K-$K_4$ alone, and a 1:1 molar ratio mixture of the two peptides, each with a final peptide concentration of 1 mM dissolved in DDI water and pH adjusted to 7 using a dilute solution of NaOH. For the analyses, 350 µL of each sample was loaded into a Beckman XL-I Analytical Ultracentrifuge cell and spun at 40,000 rpm for 3 hours at 20° C., with data collected using interference optics. The raw data was then processed using DCDT+2.2.1 software to obtain g(s*) distribution. Theoretical distribution (sum of individual peptide distribution) was obtained using OriginLab v. 7.0 software. The results are shown in FIG. 11.

The data of the N-acetyl capped peptides dissolved in DDI water shows a reproducible peptide association with an apparent S value of 8 for the peptide mixture, and around 6 and 10 for bis($h_5$)-K-$K_4$ and bis($h_9$)-K-$K_4$, respectively. Theoretically, if there were no association between the two different peptides, one would expect to see a sedimentation distribution that should correspond to the open circles in FIG. 11, which is basically the sum of the individual peptide distributions. Instead, the peptide mixture results in a sharper peak with an apparent S value of 8. This sharper peak corresponds to a new sedimenting species that most likely arises due to the interaction/association of the two different peptides with an undetermined stoichiometry. The shape of the distribution curve for the peptide mixture, as compared to the individual peptides also suggests that the peptides when mixed together are more stable and are more uniform as compared with the peptides when dissolved independently (i.e., bis($h_9$)-K-$K_4$ alone or bis($h_5$)-K-$K_4$ alone).

Example 6

Tryptophan Encapsulation

In this procedure, the amino acid tryptophan, which is a relatively small molecule with a molecular weight of 204.23 Da, was encapsulated using vesicles formed from the N-acetyl capped peptides. Advantageously, the intrinsic fluorescence of tryptophan can be followed by exciting it at 280 nm. Stock solutions of bis($h_9$)-K-$K_4$ and bis($h_5$)-K-$K_4$ dissolved in DDI water were mixed together using the protocol described in Example 4 above to achieve a final concentration of 1.6 mM of each peptide in the mixture and 500 µL final volume. The sample was then dried by spinning in a speed vacuum for about 3 hours until almost all of the solvent was removed. The dried sample was then rehydrated with either plain DDI water or a 2.2 mM solution of L-tryptophan dissolved in DDI water. The pH of the sample was adjusted to 5 using a dilute solution of NaOH. A third sample was prepared as a control where appropriate amounts of L-tryptophan were added 2 hours after rehydrating the dried vesicle sample in DDI water.

The samples we then separated from the free tryptophan using a Sephadex G-50 spin column. All samples were loaded onto separate spin columns prepared using Sephadex G-50 (GE Healthcare) in a 5 mL plastic syringe. Next, 500 µL fractions were collected by spinning the columns in a bench top centrifuge at 1,500 rpm for 2 min. About 30 fractions were collected for each sample and the fluorescence emission spectra of the eluted fractions was measured using a CARY Eclipse spectrofluorometer (Varian, Inc.) in a quartz cuvette using the following parameters:

| | |
|---|---|
| pathlength | 1 cm |
| excitation wavelength | 280 nm |
| emission wavelength | 290-500 nm |
| scan rate | 120 nm/min. |
| slit width | 2.5 nm |

All experiments were repeated at least three times. The results are shown in FIG. 12.

Figure 12:
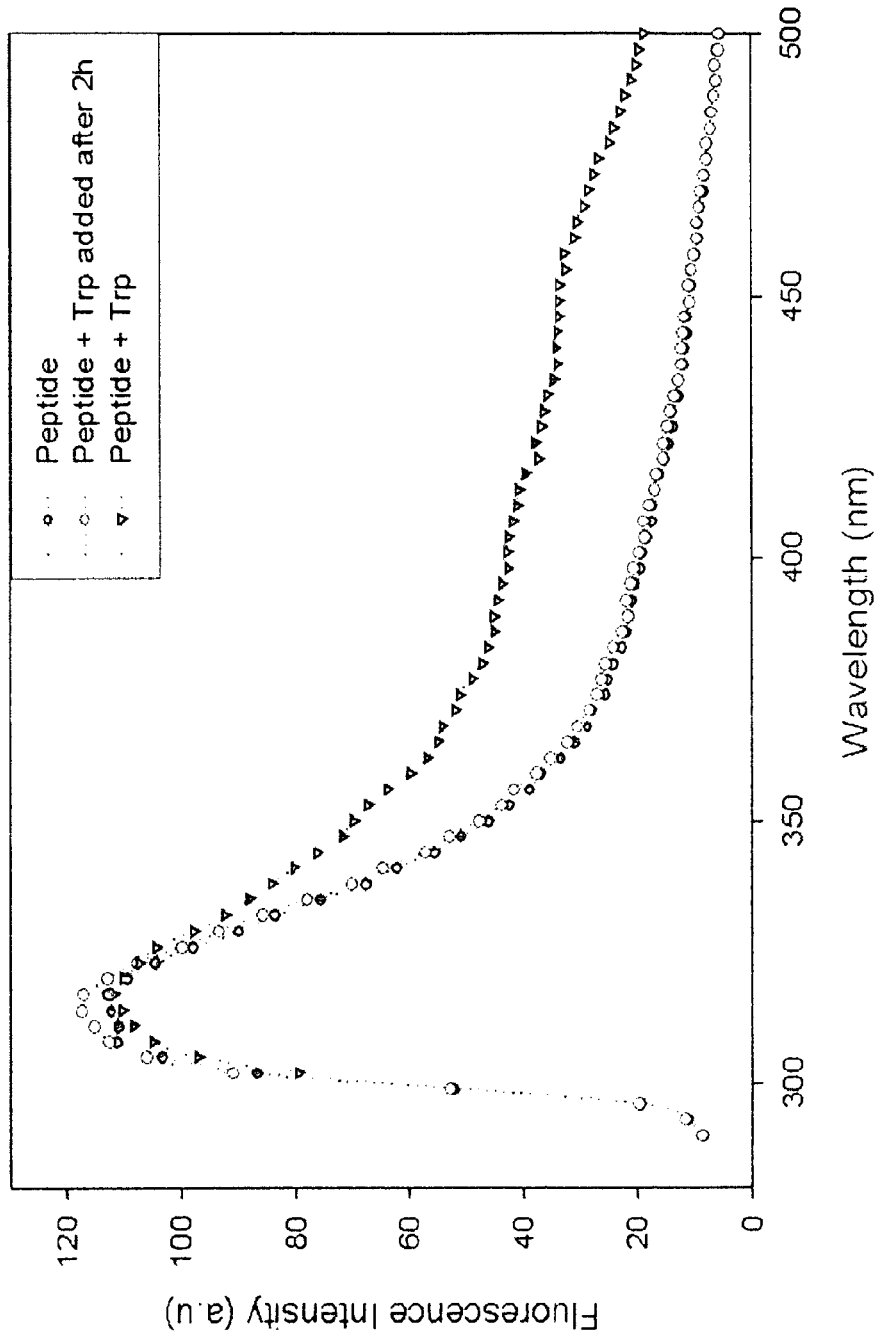
FIG. 12 is a graph of the fluorescence emission spectra from the tryptophan encapsulation experiment in Example 6.

FIG. 12 shows the fluorescence emission spectra of an eluted fraction of the three different samples. Emission spectra of the fractions which had no tryptophan and the fraction with tryptophan added 2 hours after vesicle formation show similar spectra, while there is a noticeable shoulder for the fraction which had the tryptophan added during vesicle preparation. This provides further evidence that the inventive vesicles are hollow (as opposed to having a solid core) and are capable of trapping small molecules. If the tryptophan molecules were simply lying on the outer surface of the vesicles instead of inside the vesicles, the results would have been expected to be similar to samples where the tryptophan was added 2 hours after vesicle formation. However, the shoulder for the fraction where tryptophan was added during vesicle formation seems to confirm that tryptophan is indeed trapped inside the vesicles and hence eluting along with the peptide during separation.

Example 7

Cell Culture Experiments

Human Lens Epithelial (HLE) cells were obtained from Dr. Dolores Takemoto's lab (Kansas State University). These adherent cells were grown to roughly 80% confluence on coverslips placed in 12 well plates with 1 ml Dulbecco's Modified Eagle Medium (DMEM), Stock solutions of bis($h_9$)-K-$K_4$ and bis($h_5$)-K-$K_4$ dissolved in DDI water were mixed together using the protocol described in Example 4 to achieve a final concentration of 0.025 mM of each peptide in the mixture and 600 µL final volume. The sample was then dried by spinning in a speed vacuum for about 3 hours until almost all of the solvent was removed. The dried sample was then rehydrated with a 0.5 mM solution of the fluorescent dye 5,6-carboxyfluorescein (MW=376.3 Da) dissolved in DDI water. The pH of the sample was adjusted to 7.4 using a dilute solution of NaOH. Next, 500 µL of the DMEM was replaced with the peptide vesicle solution loaded with 5,6-carboxyfluorescein. The cells were then allowed to grow at 37° C. under 5% $CO_2$. At 4 hours and 12 hours after incubation with dye-loaded vesicles, the cells were washed twice with phosphate buffered saline (PBS) and fixed using 0.4% paraformaldehyde. The fixed cells were then mounted on a glass slide and pictures were taken using a fluorescence microscope. Control cells were incubated with only the free fluorescent dye and no peptide vesicles, followed by washing twice with PBS and fixed with formaldehyde. The resulting images are shown in FIG. 13.

Figure 13:
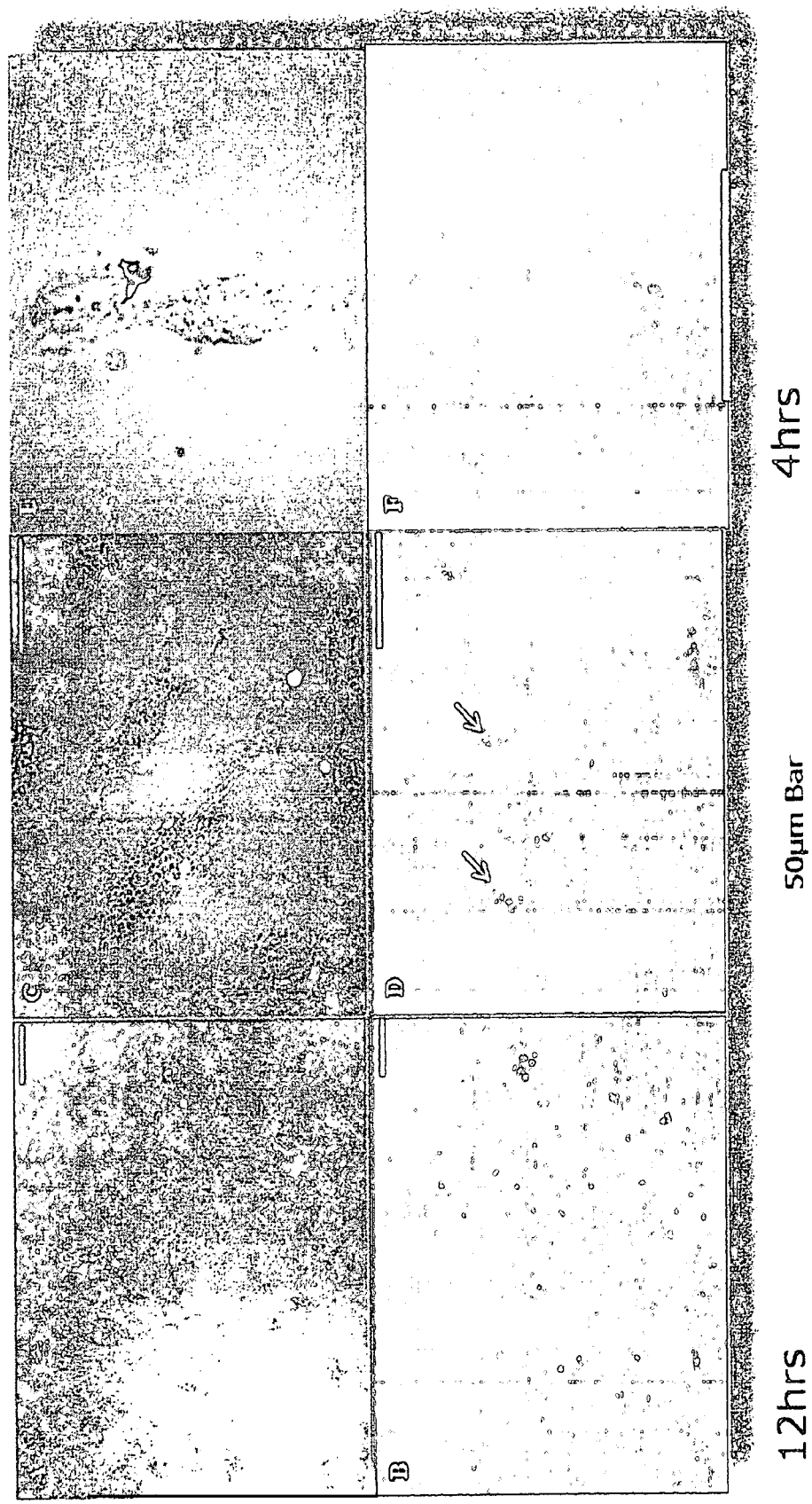
FIG. 13 depicts fluorescence images depicting the uptake of peptide vesicles loaded with 5,6-carboxyfluorescein solution by human lens epithelial cells over various periods of time.

Fluorescence images of the cells after 12 hours of incubation with the dye-loaded vesicles show that the dye is taken up by the cells and primarily accumulates at the peri-nuclear space (FIG. 13(A-D)). Images of cells taken after 4 hours of incubation with the dye-loaded vesicles show that the dye is still on the outside (FIG. 13(E-F)). Control cells that were incubated with only the free fluorescent dye showed hardly any uptake of the dye even after 12 hours (not shown). These results demonstrate that FILE cells internalize the dye only when it is prepackaged with the peptide vesicles.

Example 8

Preparation of Vesicles for Selective Cell Uptake

Figure 14:
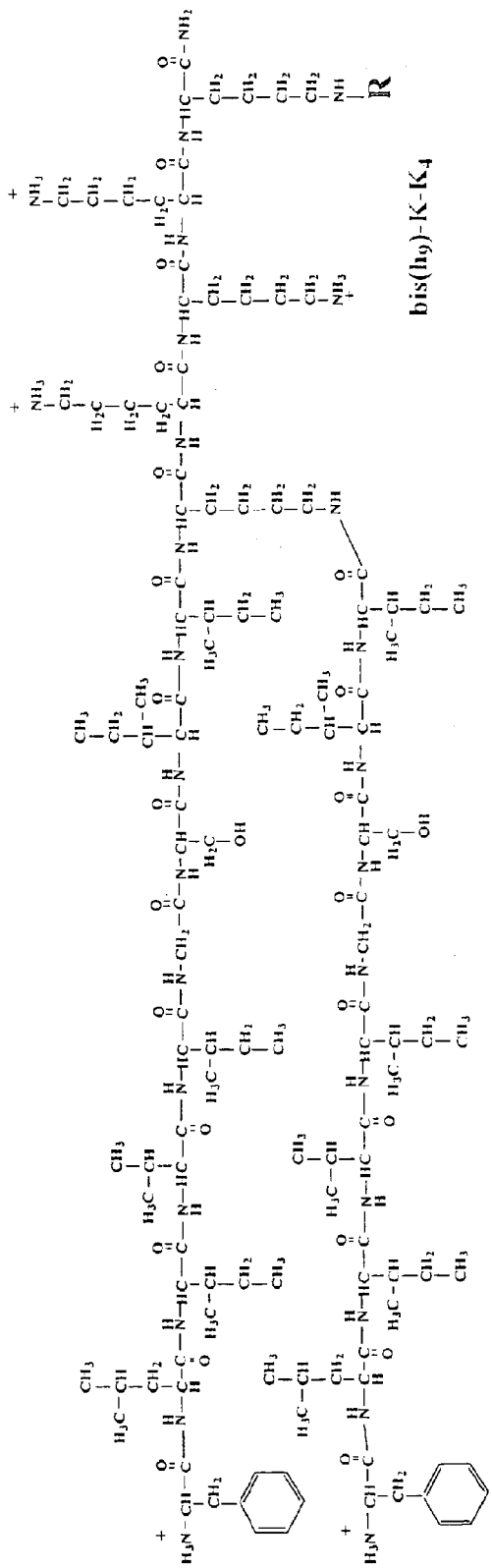
FIG. 14 illustrates bis($h_9$)-K-$K_4$ prepared with a targeting molecule represented by R.

In this Example, the preparation of vesicles with targeting molecules to enable selective cell uptake will be described. As demonstrated above, without any modification, the vesicles attach to the surface of cells in culture. There may, however, be instances where it is desired to make use of a particular endocytic pathway to get the vesicles into cells where they can deliver their contents. By covalently attaching a specific targeting molecule to the epsilon group of the C-terminal lysine (R group shown in FIG. 14) of the bis($h_9$)-K-$K_4$ sequence, the vesicles can be designed to interact with specific cell surface receptors. The R group is added at the beginning of the peptide synthesis described in Example 1. Once that group is attached the rest of the bis($h_9$)-K-$K_4$ sequence is added. Examples of the types of groups that could be added to the vesicles include cholesterol, mannose, biotin, the peptide sequence known as TAT, nucleotides, or any other suitable known surface targeting molecules, and combinations thereof. See FIG. 14.

Only a small percentage of the R-group containing sequence is added to the vesicle mixture (such as adding 1 part of the R-group containing to 9 parts of the unmodified bis($h_9$)-K-$K_4$ sequence). This, in turn, is added to the desired ratio of the bis($h_9$)-K-$K_4$ sequence in DDI water and the vesicles are allowed to form. The majority of the R-group adducted sequence will then be presented on the outer surface of the vesicle once formed where it can interact with specific cell surface receptors.

Example 9

Figure 15:
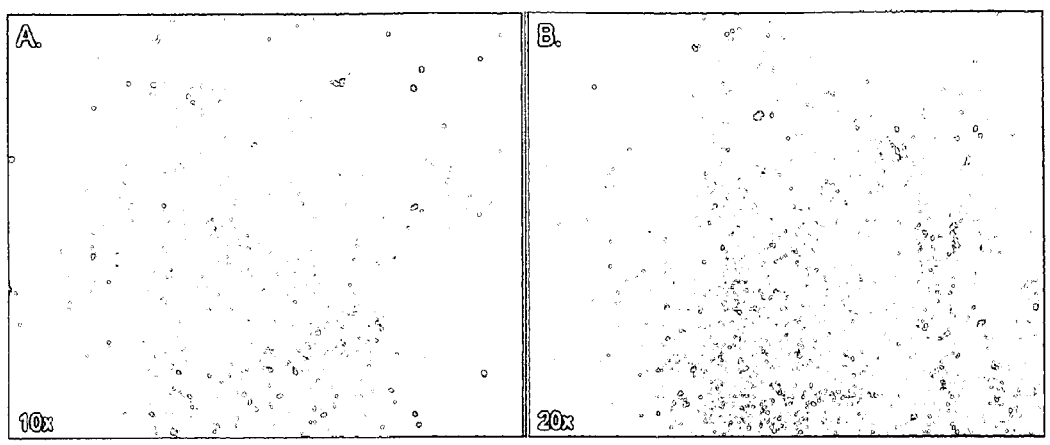
FIG. 15 shows fluorescence microscope photographs of Mouse Embryonic Fibroblast (MEF) cells transfected with plasmid DNA encapsulated in peptide vesicles and expressing Enhanced Green Fluorescence Protein (EGFP) at: A. 10× magnification; and B. 20× magnification.

DNA uptake by Mouse Embryonic Fibroblast (MEF) Cells When Presented with Peptide Vesicles In this Example, small plasmid DNA, carrying the gene for Enhanced Green Fluorescence Protein (EGFP) was delivered into MEF cells grown in 6 well cell culture plates, using peptide vesicles formed from N-acetyl capped bis($h_9$)-$K_4$ and bis($h_5$)-K-$K_4$. In order to keep the overall size of the plasmid small to facilitate better and easier packaging into peptide vesicles, a 0.732 kb fragment of the plasmid was isolated from the original plasmid (pCX-EGFP) and cloned. This fragment carried the gene (EGFP) for the protein. The plasmid (pCX-EGFP) was purchased from Addgene (Cambridge, Mass.). A 0.732 kb fragment of the plasmid, carrying the EGFP gene was isolated using SAL1 restriction enzyme and cloned using BlueScript®. Next, 100 µL of 7.3 ng/µL of this 0.732 kb fragment was encapsulated into approximately 100 µM of the peptide vesicles using the protocol described above in Example 6 for tryptophan encapsulation. The MET cells were grown to 100% confluence in 6 well cell culture plates, with DMEM growth media. These cells were treated with 100 µL of the vesicle encapsulated plasmids by adding the vesicle solution direct to the growth media, and the cells were then allowed to grow at 37° C. for 60 hours before pictures were taken using a fluorescence microscope. Control cells were treated with the naked plasmid (unencapsulated). Only cells that take up the plasmid and express the protein will fluoresce green when light of suitable wavelength is used to excite them. The MEF cells showed an enhanced uptake of the plasmid when it was delivered through peptide vesicles (FIG. 15A-B) as compared to direct uptake of naked plasmid (FIG. not shown). This is evident from the amount of fluorescence observed in the cytoplasm of the cells. These pictures show that plasmid DNA can be packaged with the peptide vesicles and successfully delivered into MEF cells. The white circles represent the green fluorescence due to the expression of EGFP in the cytoplasm.

We claim:

1. A branched, amphipathic, vesicle-forming peptide selected from the group consisting of bis(h)-K-$K_n$ and the N-acetylated derivatives thereof, where h is a hydrophobic amino acid sequence selected from the group consisting of FLIVIGSII(SEQ ID NO: 3), FLIVI (SEQ ID NO: 4), and VFFIVIL(SEQ ID NO: 5), -K- is a branched lysine residue, K is lysine, and n is from about 1 to about 7, wherein $K_n$ is a C-terminal hydrophilic component and wherein a targeting moiety is optionally attached to said hydrophilic component.

2. An aqueous composition comprising a first amphipathic, branched, vesicle-forming peptide and a second amphipathic, branched, vesicle-forming peptide, wherein said first and second peptides each consist of a respective C-terminal hydrophilic component, a branch point, two respective N-terminal hydrophobic components, an optional targeting moiety attached to said hydrophilic component, and an optional acetyl group on the N-terminal end of each hydrophobic component, said hydrophobic components being selected from the group consisting of FLIVIGSII (SEQ ID NO: 3), FLIVI (SEQ ID NO: 4), and VFFIVIL (SEQ ID NO: 5), wherein said hydrophobic components are each coupled to said branch point, and said branch point is coupled to said hydrophilic component, and wherein said first peptide has a first number of amino acid residues, and said second peptide has a second number of amino acid residues, said first number of amino acid residues being different from said second number of amino acid residues.

3. The composition of claim 2, said composition further comprising a solvent selected from the group consisting of 2,2,2-trifluoroethanol, tetrahydrofuran, and acetonitrile.

4. The composition of claim 3, wherein said solvent is 2,2,2-trifluoroethanol, said composition comprising from about 20% v/v to about 80% v/v 2,2,2-trifluoroethanol.

5. The composition of claim 2, wherein the molar ratio of said first peptide to said second peptide in said composition is from about 1:10 to about 10:1.

6. The composition of claim 2, wherein said hydrophilic component is KKKK (SEQ ID NO: 1).

7. The composition of claim 2, wherein said first peptide is selected from one of the group consisting of bis(h)-K-$K_n$ and the N-acetylated derivatives thereof, where h is an amino acid sequence selected from the group consisting of FLIVIGSII (SEQ ID NO: 3), FLIVI (SEQ ID NO: 4), and VFFIVIL (SEQ ID NO: 5), -K- is a branched lysine residue, K is lysine, and n is from about 1 to about 7, and said second peptide is selected from another of the group consisting of bis(h)-K-$K_n$ and the N-acetylated derivatives thereof, where h is an amino acid sequence selected from the group consisting of FLIVIGSII (SEQ ID NO: 3), FLIVI (SEQ ID NO: 4), and VFFIVIL (SEQ ID NO: 5), -K- is a branched lysine residue, K is lysine, and n is from about 1 to about 7.

8. The composition of claim 2, wherein said first peptide is bis($h_5$)-K-$K_4$, and said second peptide is bis($h_9$)-K-$K_4$, where -K- is a branched lysine residue, K is lysine, $h_9$ is FLIVIGSII (SEQ ID NO: 3) and $h_5$ is FLIVI (SEQ ID NO 4).

9. The composition of claim 2, wherein the concentration of said first peptide in said composition is from about 1 mM to about 5 mM.

10. The composition of claim 2, wherein the concentration of said second peptide in said composition is from about 1 mM to about 5 mM.

11. The composition of claim 2, wherein said composition has a pH of from about 4 to about 9.

12. The composition of claim 2, wherein said composition is substantially free of lipids or phospholipids.

13. A method of encapsulating an active agent comprising:
    (a) dispersing or dissolving said active agent in an aqueous composition according to claim 2; and
    (b) allowing said dispersion or solution to stand for at least 2 hours to form vesicles having a bilayer membrane comprising said first and second amphipathic, branched peptides and encapsulating said active agent.

14. The method of claim 13, wherein said active agent is selected from the group consisting of therapeutic molecules, radioactive isotopes, RNA oligomers, quantum dots, DNA plasmids, enzymes, poisons, toxins, secondary messengers, dyes, and combinations thereof.

15. The method of claim 13, said bilayer membrane having interior and exterior layers and defining a liquid-receiving interior space, wherein said membrane comprises said first amphipathic, branched peptide having a first number of amino acid residues, and said second amphipathic, branched peptide having a second number of amino acid residues.

16. The method of claim 15, wherein each of said hydrophobic components are oriented inward defining the core of said bilayer member and each of said hydrophilic components are oriented outward from said bilayer membrane core, thereby defining interior and exterior surfaces of said interior and exterior layers of the bilayer membrane.

17. The method of claim 16, wherein said bilayer interior layer comprises said first peptide and said bilayer exterior layer comprises said second peptide, the core of said bilayer member comprising interlocking hydrophobic components wherein the hydrophobic components of said first peptide in the interior layer interdigitate with the hydrophobic components of said second peptide in the exterior layer in an antiparallel beta-sheet structure.

18. The method of claim 15, wherein said bilayer membrane is substantially free of lipids or phospholipids.

19. The method of claim 15, wherein said peptide vesicles further comprise a targeting moiety on the exterior surface of said membrane.

20. The method of claim 19, wherein said targeting moiety is selected from the group consisting of mannose, cholesterol, biotin, TAT sequence, insulin, nucleotides, and combinations thereof.

21. The method of claim 15, wherein said first peptide is bis($h_5$)-K-$K_4$, and said second peptide is bis($h_9$)-K-$K_4$, where -K- is a branched lysine residue, K is lysine, $h_9$ is FLIVIGSII (SEQ ID NO: 3) and $h_5$ is FLIVI (SEQ ID NO 4).

22. A method of targeting delivery of an active agent to a region of a patient comprising administering to said patient vesicles formed by the method according to claim 15, wherein said vesicles further comprises a targeting moiety on the exterior surface of said membrane.

\* \* \* \* \*

SEQUENCE LISTING

```
<160> NUMBER OF SEQ ID NOS: 7

<210> SEQ ID NO 1
<211> LENGTH: 4
<212> TYPE: PRT
<213> ORGANISM: Artificial Sequence
<220> FEATURE:
<223> OTHER INFORMATION: Synthetic sequence

<400> SEQUENCE: 1

Lys Lys Lys Lys
1
```

```
<210> SEQ ID NO 2
<211> LENGTH: 22
<212> TYPE: PRT
<213> ORGANISM: Homo sapiens

<400> SEQUENCE: 2

Asp Pro Trp Asn Val Phe Asp Phe Leu Ile Val Ile Gly Ser Ile Ile
1               5                   10                  15

Asp Val Ile Leu Ser Glu
            20

<210> SEQ ID NO 3
<211> LENGTH: 9
<212> TYPE: PRT
<213> ORGANISM: Artificial Sequence
<220> FEATURE:
<223> OTHER INFORMATION: Synthetic sequence designed from internal
      fragment of human dihydropyridine sensitive L-type calcium channel
      segment CaIVS3.

<400> SEQUENCE: 3

Phe Leu Ile Val Ile Gly Ser Ile Ile
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic sequence designed from internal
      fragment of human dihydropyridine sensitive L-type calcium channel
      segment CaIVS3.

<400> SEQUENCE: 4

Phe Leu Ile Val Ile
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic sequence

<400> SEQUENCE: 5

Val Phe Phe Ile Val Ile Leu
1               5

<210> SEQ ID NO 6
<211> LENGTH: 15
<212> TYPE: PRT
<213> ORGANISM: Artificial Sequence
<220> FEATURE:
<223> OTHER INFORMATION: Synthetic sequence

<400> SEQUENCE: 6

Lys Lys Lys Phe Leu Ile Val Ile Gly Ser Ile Ile Lys Lys Lys
1               5                   10                  15

<210> SEQ ID NO 7
<211> LENGTH: 11
<212> TYPE: PRT
```

```
<213> ORGANISM: Artificial Sequence
<220> FEATURE:
<223> OTHER INFORMATION: Synthetic sequence

<400> SEQUENCE: 7

Lys Lys Lys Phe Leu Ile Val Ile Lys Lys Lys
1               5                   10
```